United States Patent [19]

Akopov et al.

[11] Patent Number: 5,484,451
[45] Date of Patent: Jan. 16, 1996

[54] ENDOSCOPIC SURGICAL INSTUMENT AND STAPLES FOR APPLYING PURSE STRING SUTURES

[75] Inventors: Ernest Akopov; Vytchesalv Astashov; Nikolai Tvorogov; Sergei Udalov, all of Moscow, Russian Federation

[73] Assignee: Ethicon, Inc., Somerville, N.J.

[21] Appl. No.: 117,260

[22] Filed: Sep. 3, 1993

Related U.S. Application Data

[63] Continuation-in-part of Ser. No. 881,010, May 8, 1992, Pat. No. 5,242,457.

[51] Int. Cl.$^6$ ................................................. A61B 17/00
[52] U.S. Cl. ........................... 606/139; 606/144; 606/151; 227/175.1; 227/176.1
[58] Field of Search .................................. 606/151, 153, 606/150, 139, 144, 148, 219, 220; 227/175–177, 181, 182, 901, 19; 673/1, 12

[56] References Cited

U.S. PATENT DOCUMENTS

| | | | |
|---|---|---|---|
| 4,345,600 | 8/1982 | Rothfuss | 606/148 |
| 4,749,114 | 6/1988 | Green | 227/19 |
| 4,773,420 | 9/1988 | Green | 227/178 |
| 4,821,939 | 4/1989 | Green | 227/19 |
| 5,129,570 | 7/1992 | Schulze et al. | 227/19 |
| 5,188,636 | 2/1993 | Fedotov | 606/151 |
| 5,242,457 | 9/1993 | Akopov et al. | 606/144 |

*Primary Examiner*—Stephen C. Pellegrino
*Assistant Examiner*—Jeffrey A. Schmidt
*Attorney, Agent, or Firm*—Paul A. Coletti

[57] ABSTRACT

A surgical staple for securing a purse string suture to human tissue comprises a staple body of deformable material formed into a loop through which the purse string suture is threaded. The staple body includes a pair of legs which are deformable into an overlapping configuration upon insertion into the tissue to secure the staple body and the purse string suture to the tissue. Alternatively, the staple body includes two or more legs including barbed ends for anchoring the legs to the tissue. To secure the purse string suture, a plurality of staples is positioned about the periphery of the tubular section of tissue, the purse string suture is threaded through the loops in the staples, and the staples are driven into the tissue to secure the purse string suture thereto. In addition, surgical instruments for open surgery and endoscopic surgery are provided for applying the staples and the purse string suture to the tissue. The instruments include a pair of staple cartridges each having a row of staple receiving slots intersected by an elongated central slot which allows the purse string suture to be attached to the staples in the cartridge prior to the operation of the instrument.

15 Claims, 28 Drawing Sheets

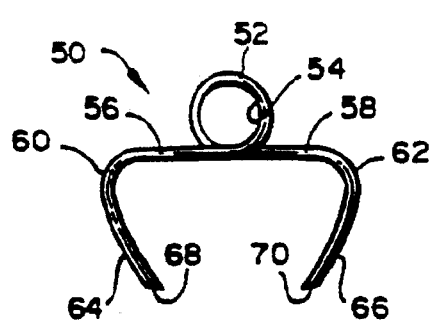
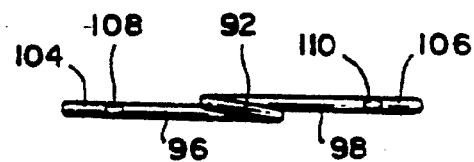
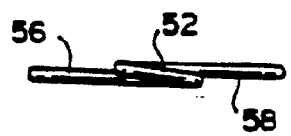
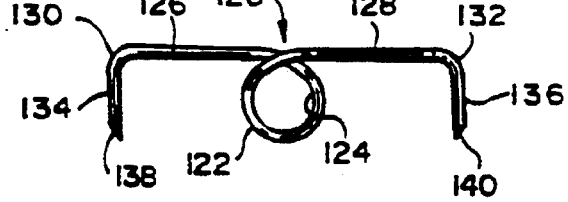
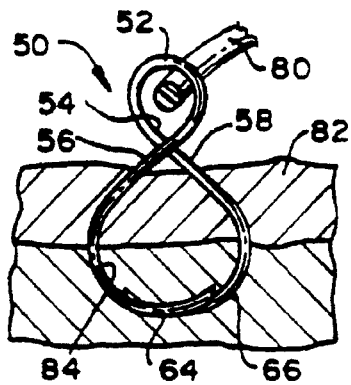
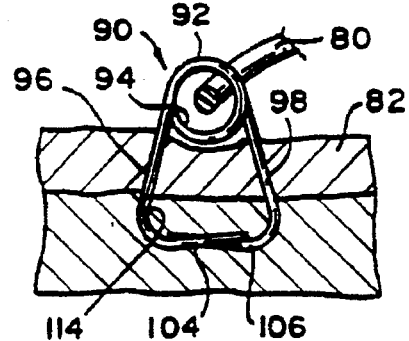
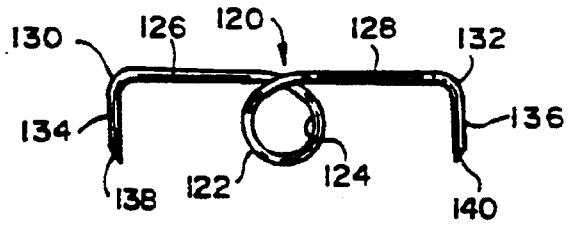
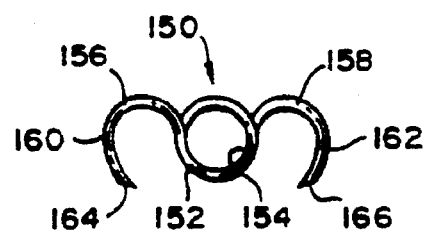
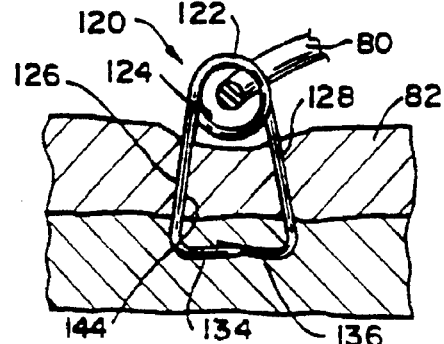
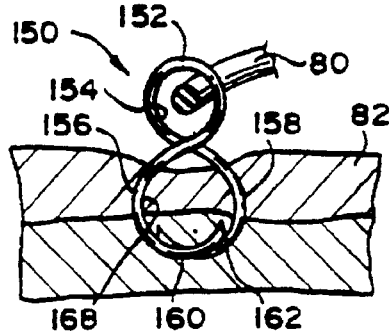

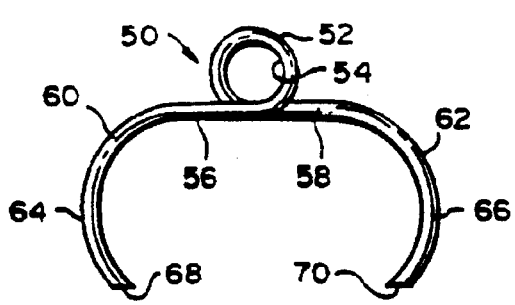
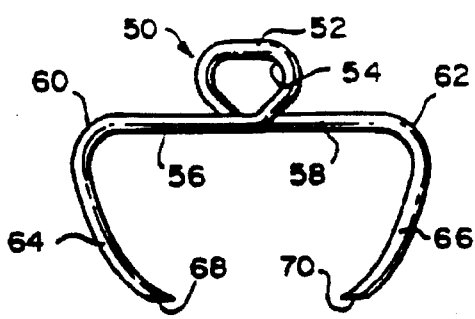
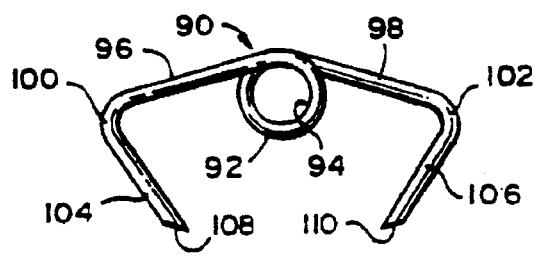
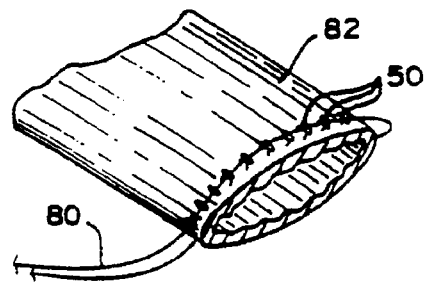
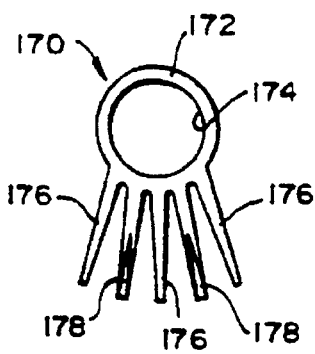
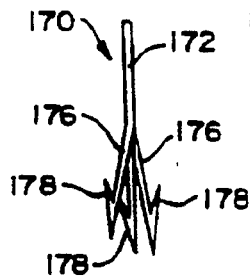
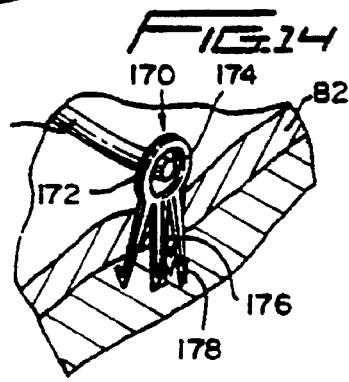
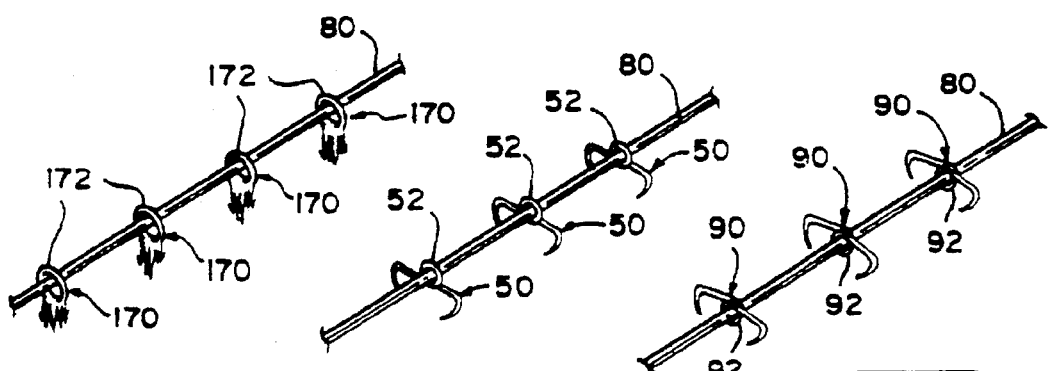

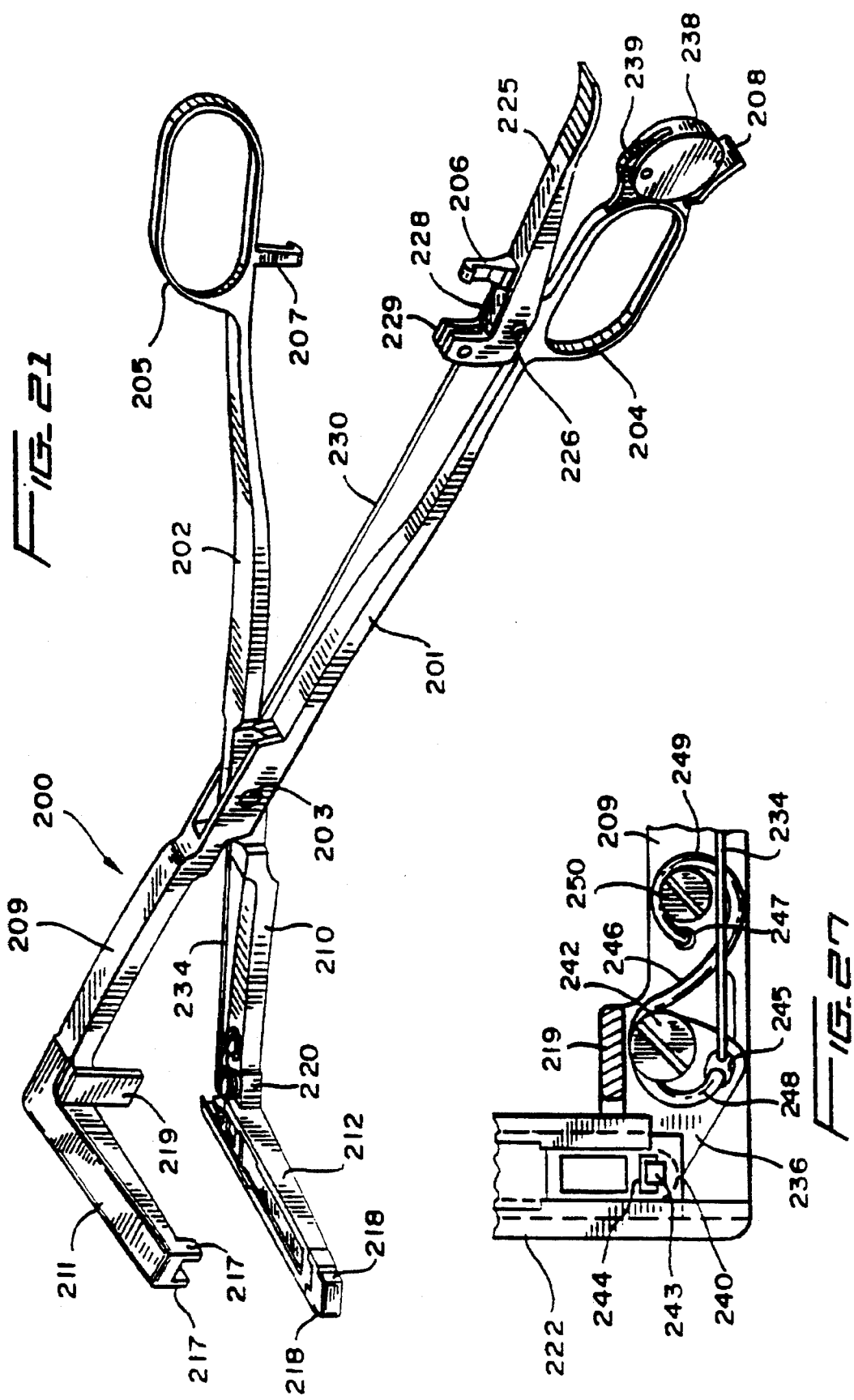

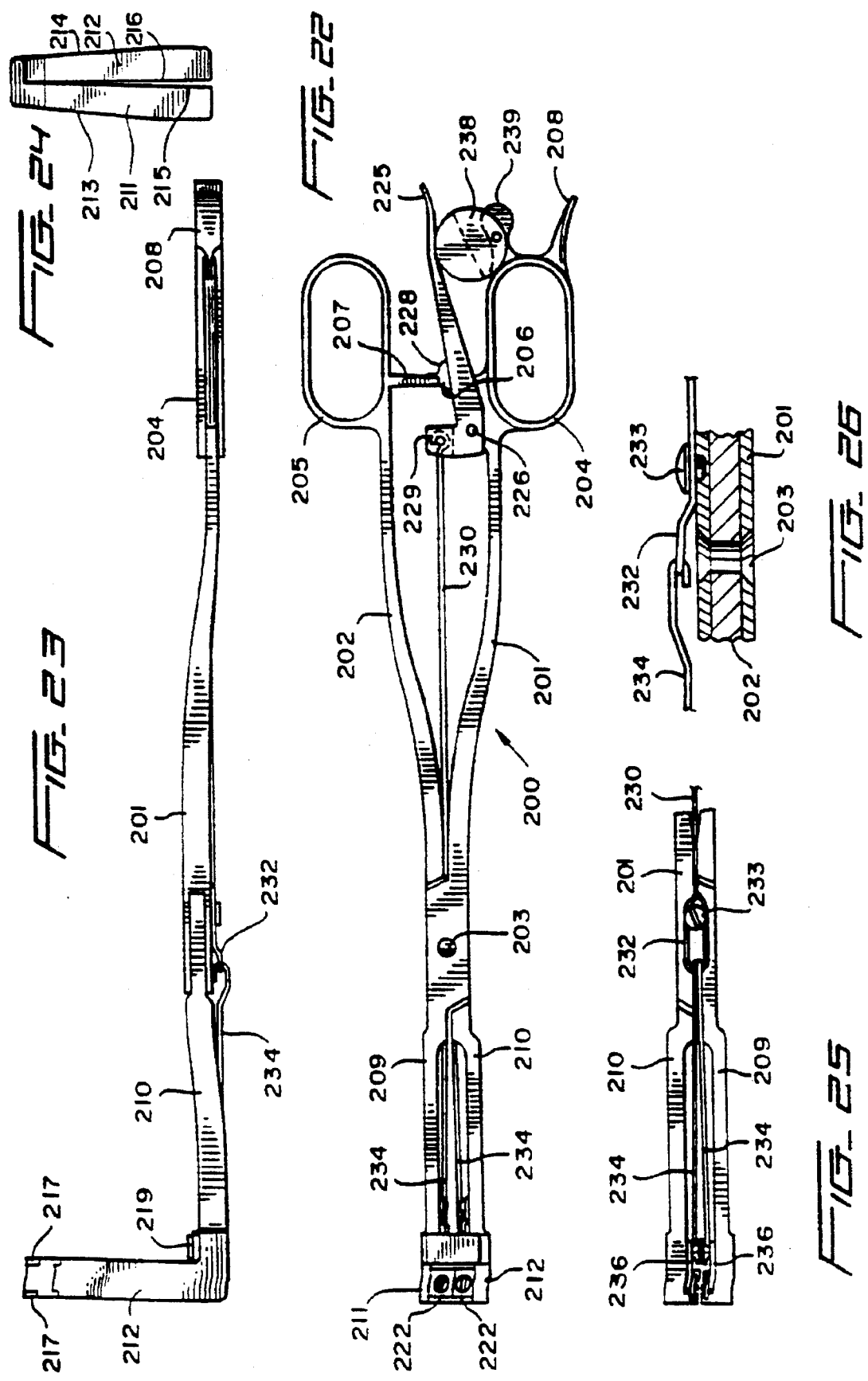

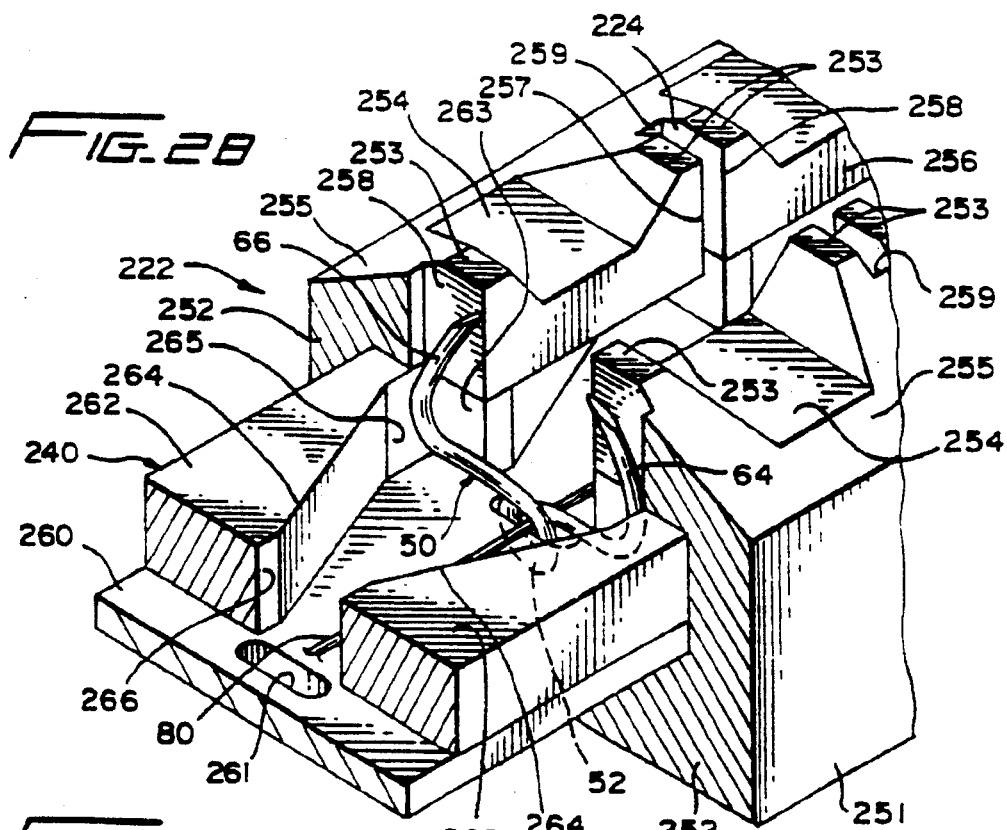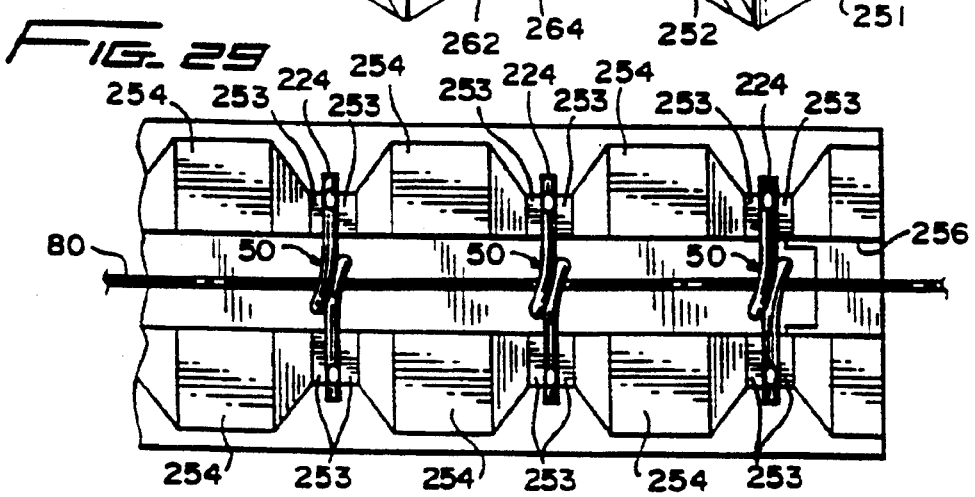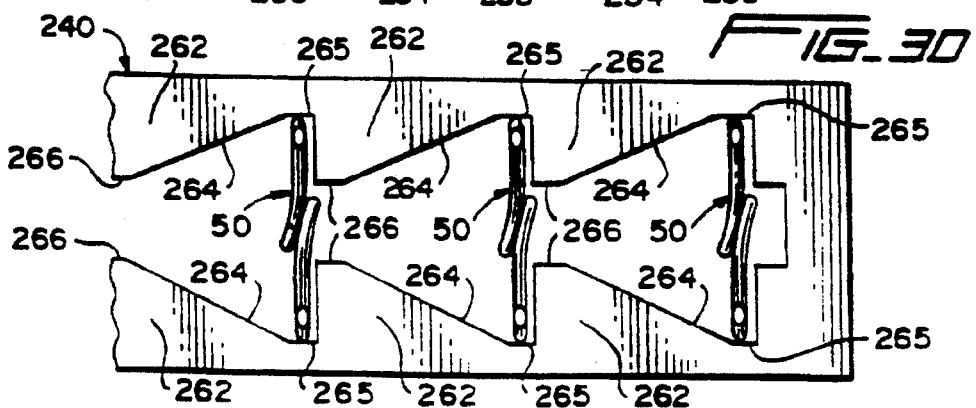

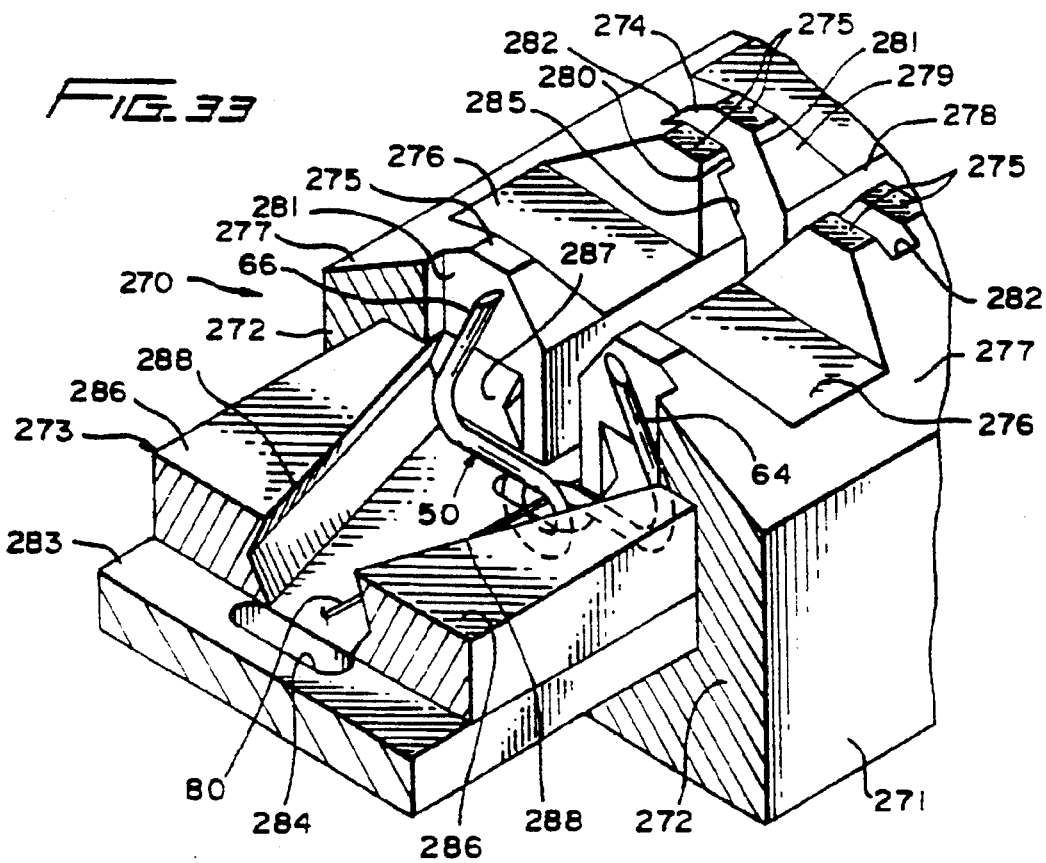
FIG. 33
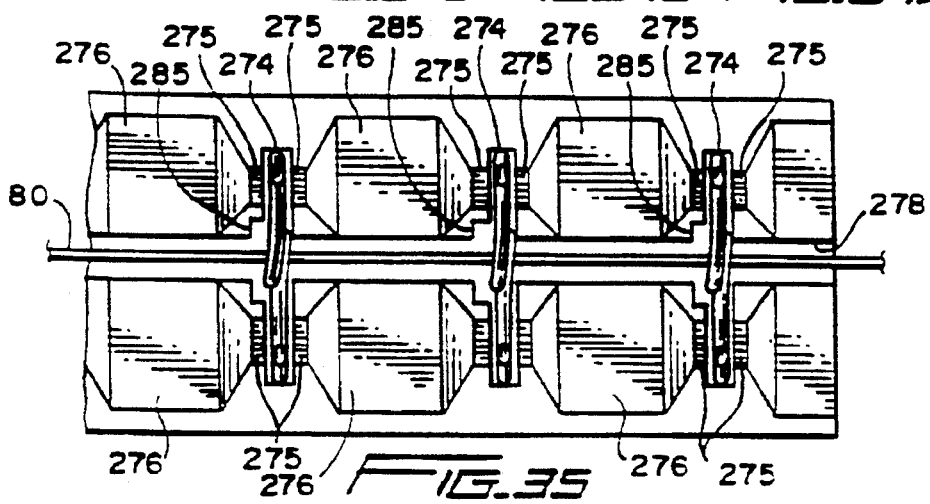
FIG. 34A  FIG. 34B  FIG. 34C  FIG. 34D
FIG. 35

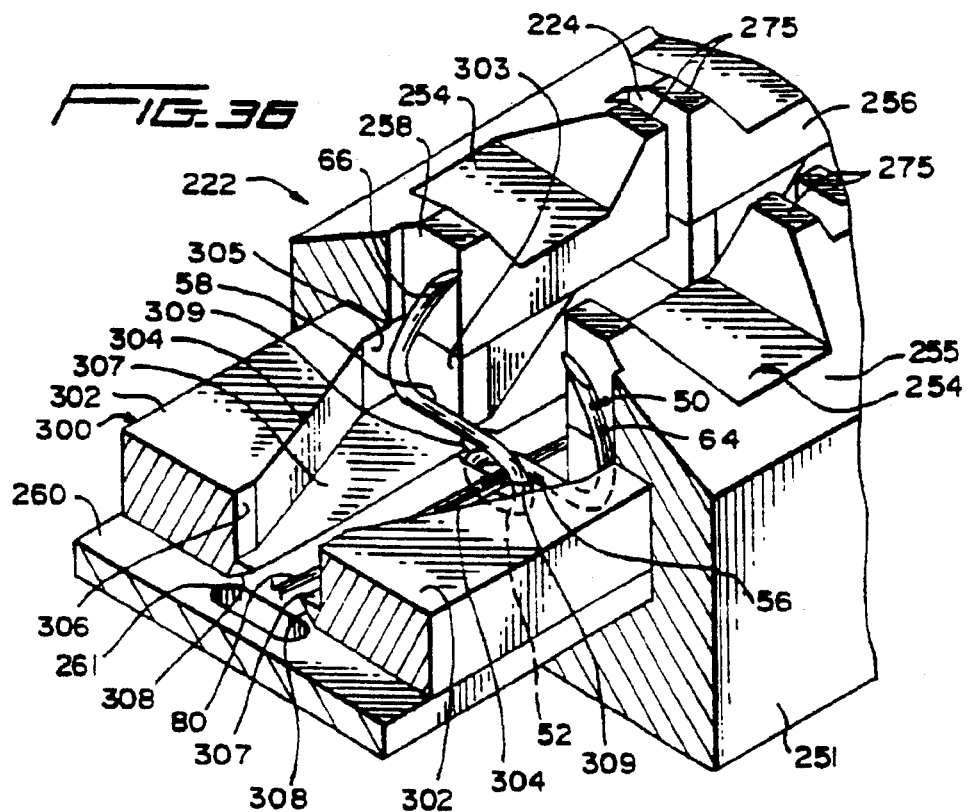
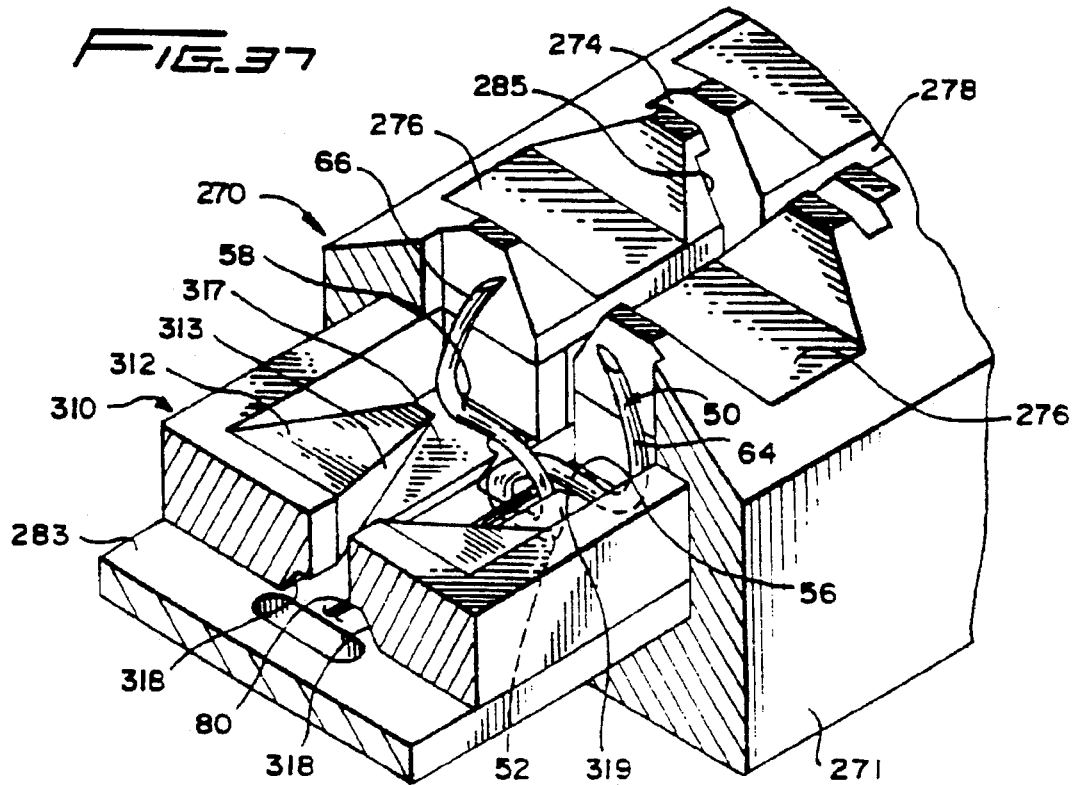

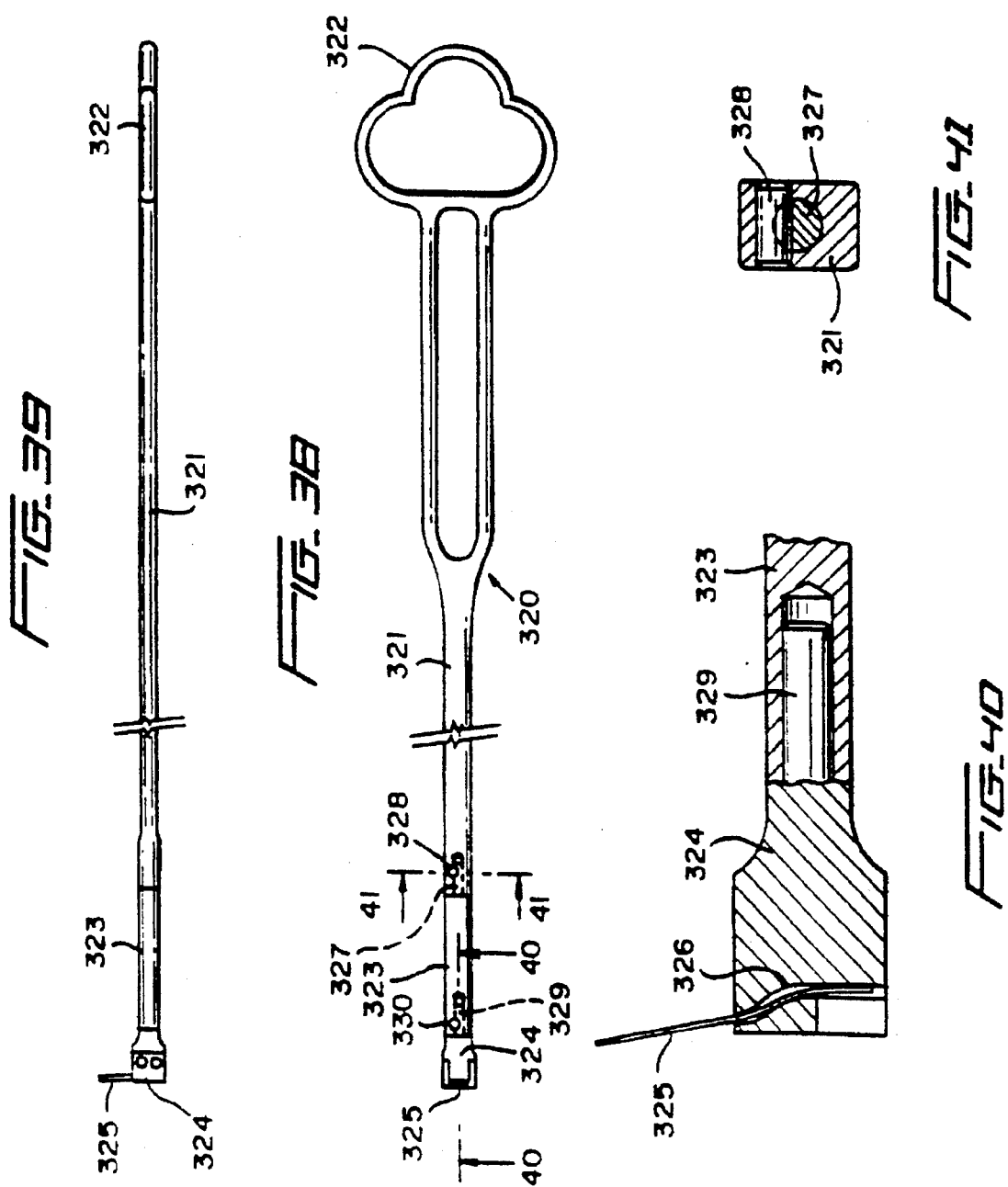

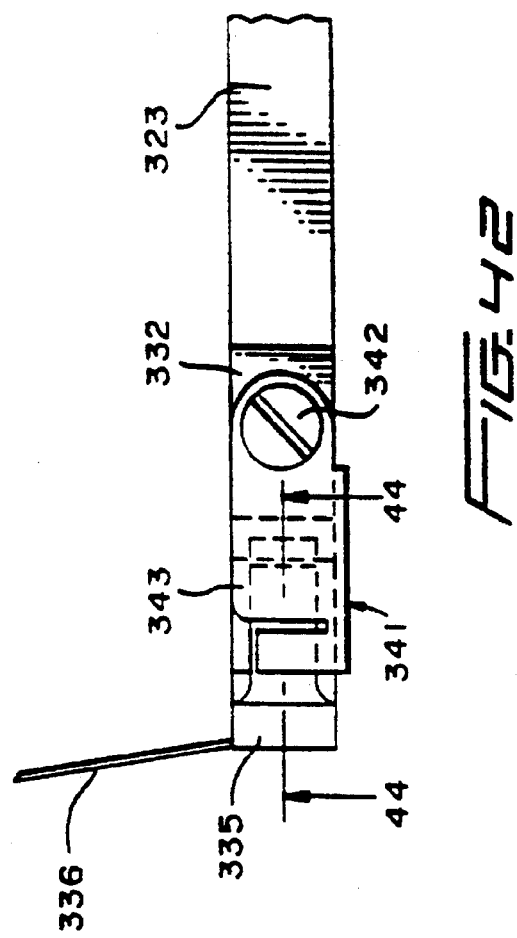
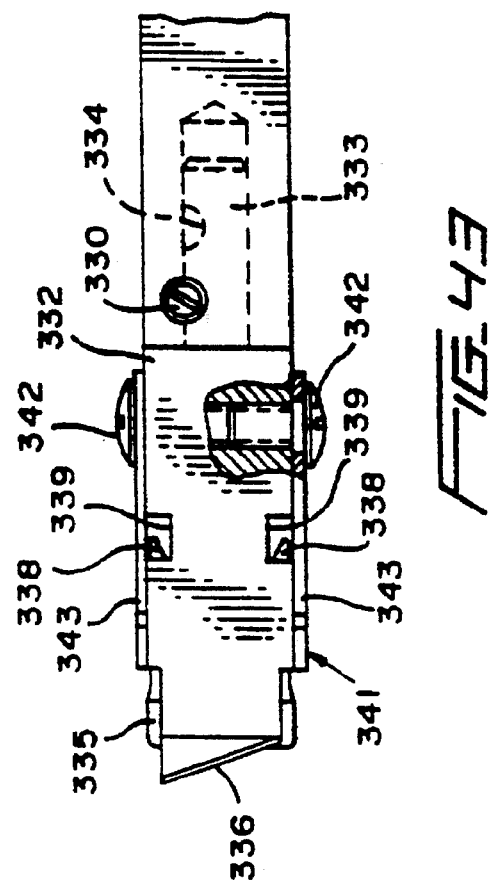
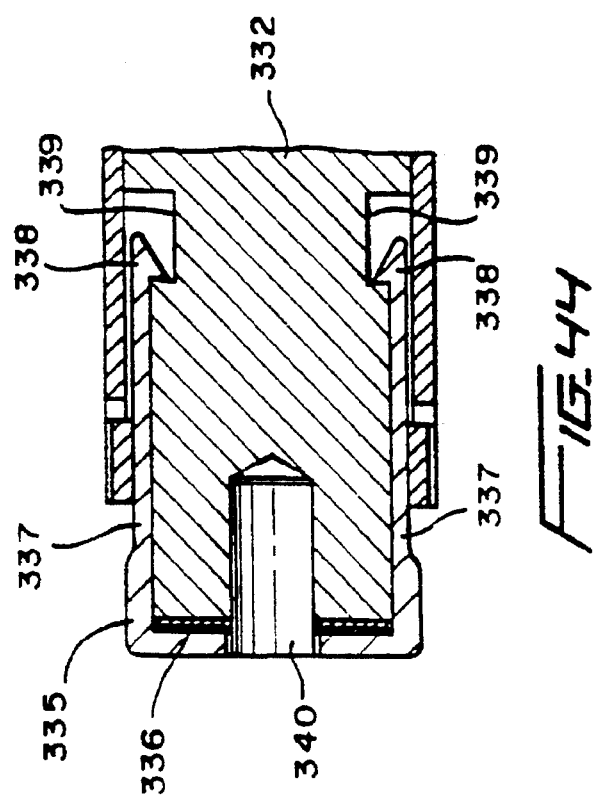

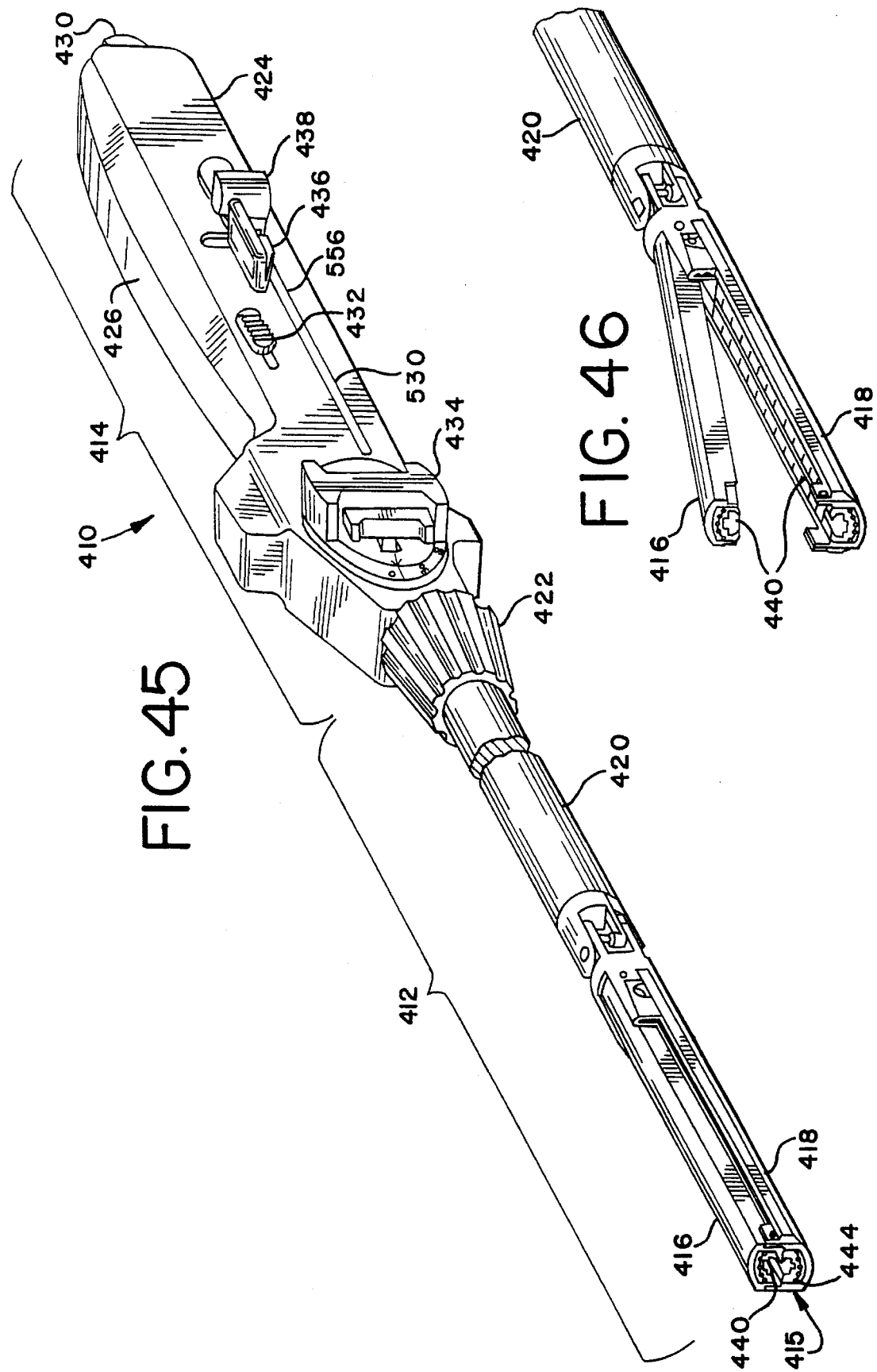

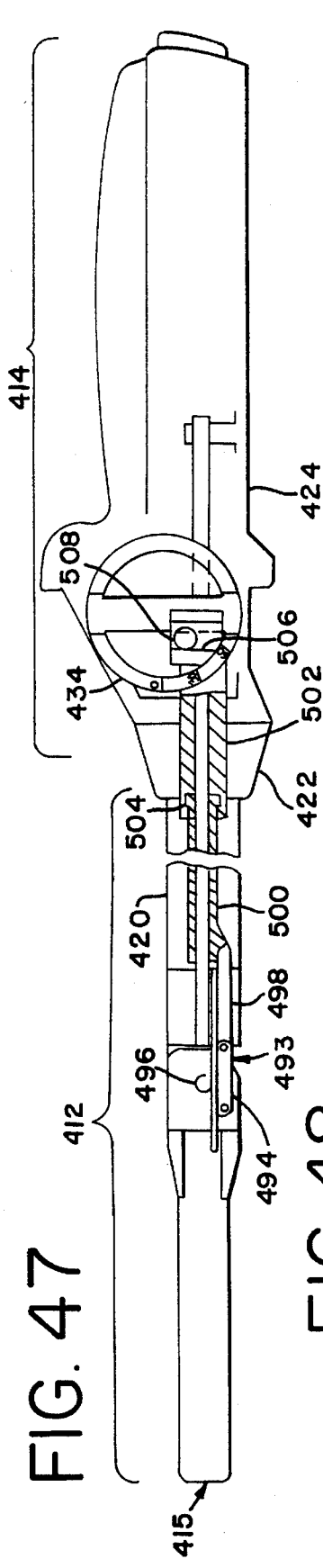
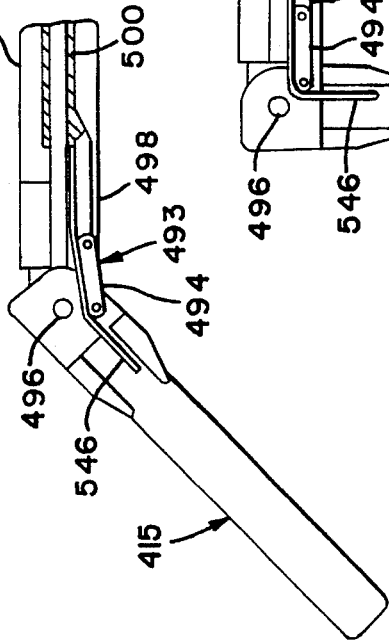
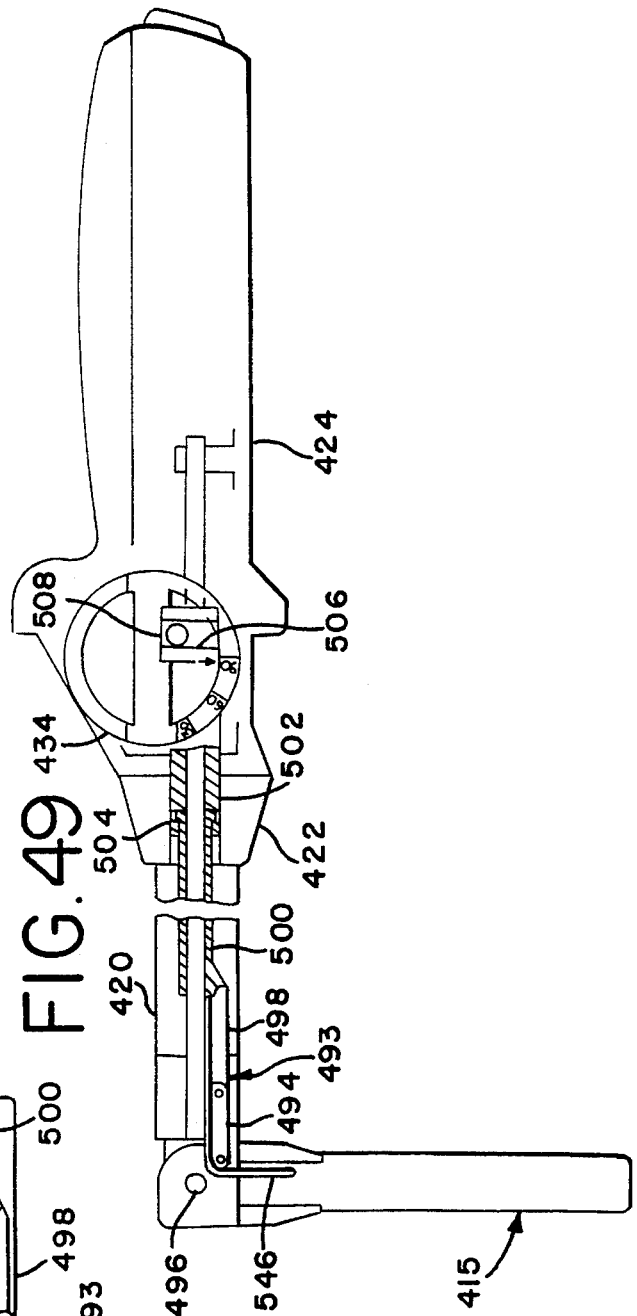
FIG. 47
FIG. 48
FIG. 49

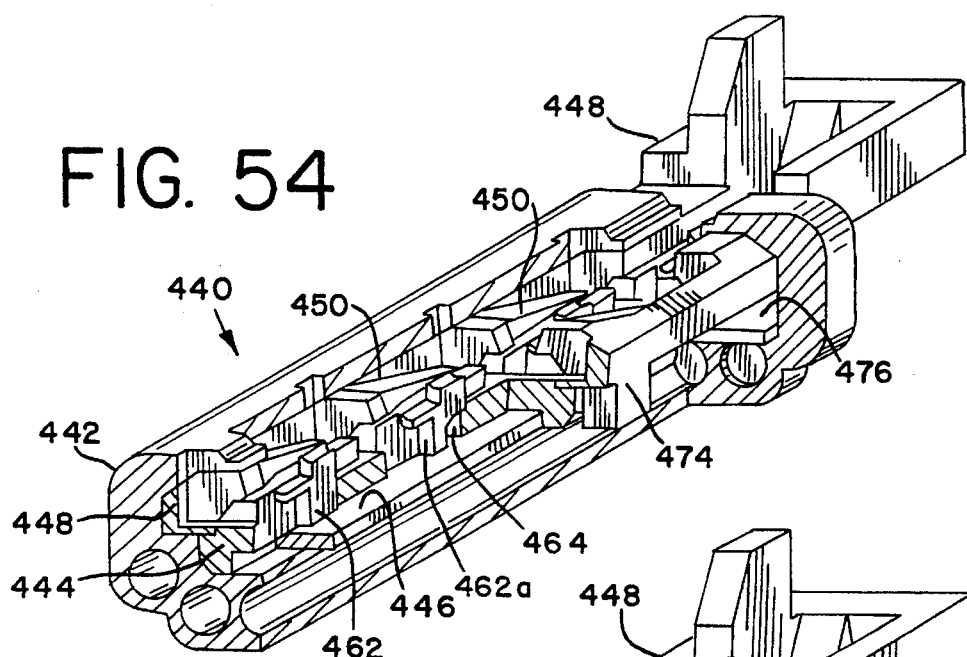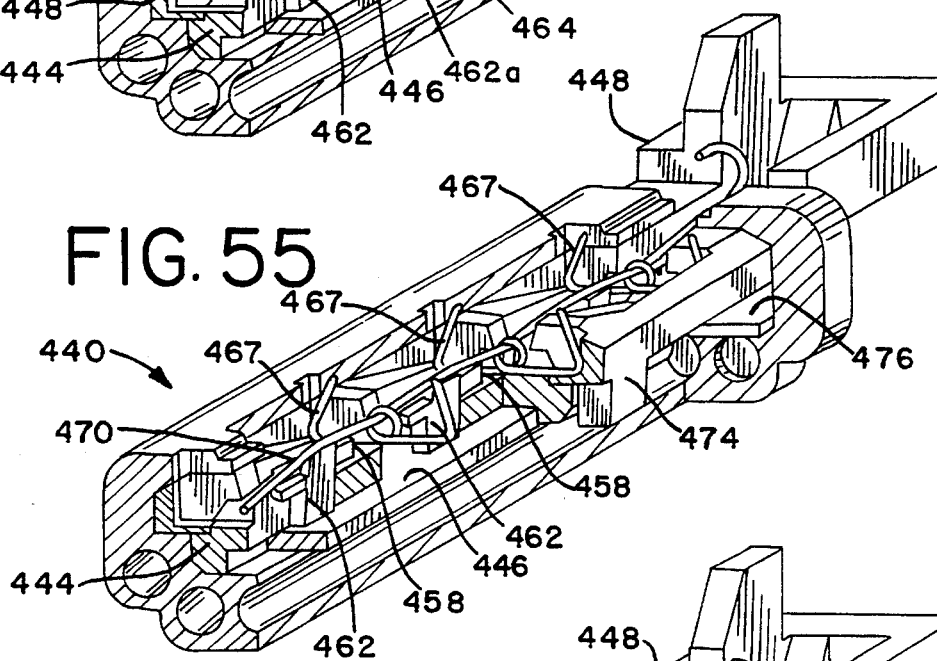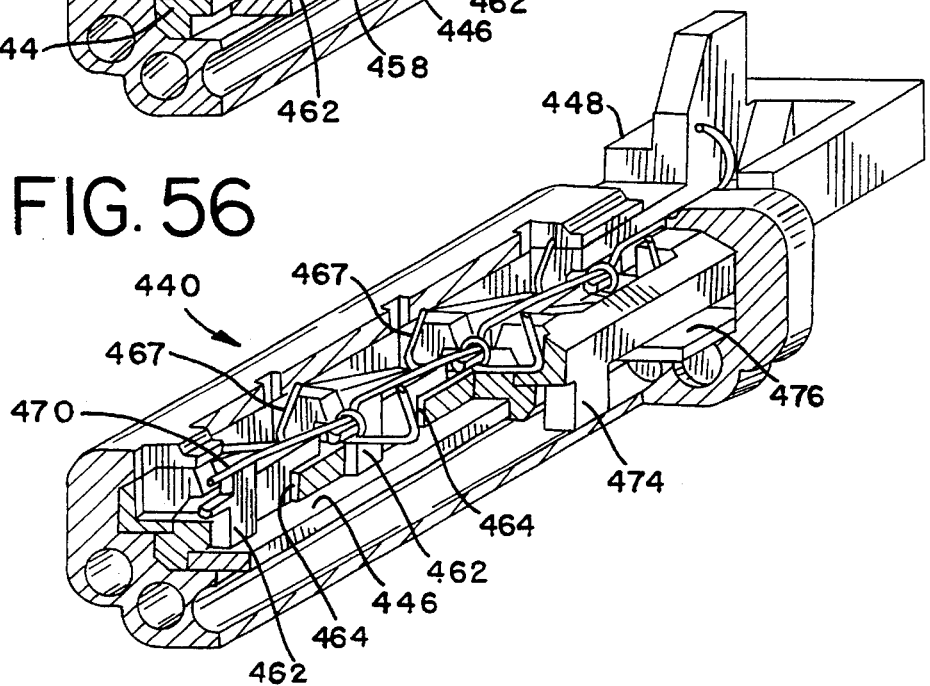

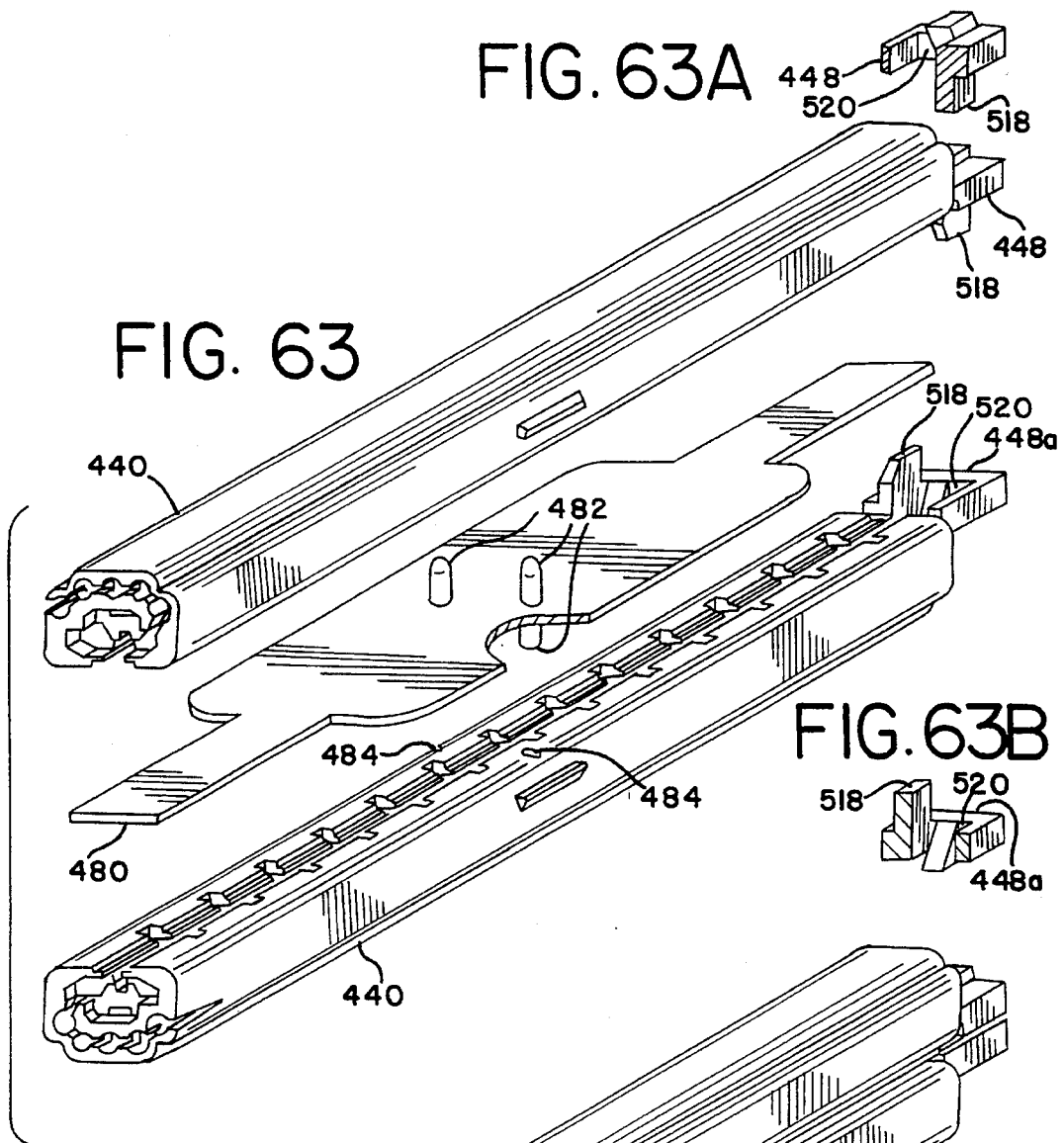

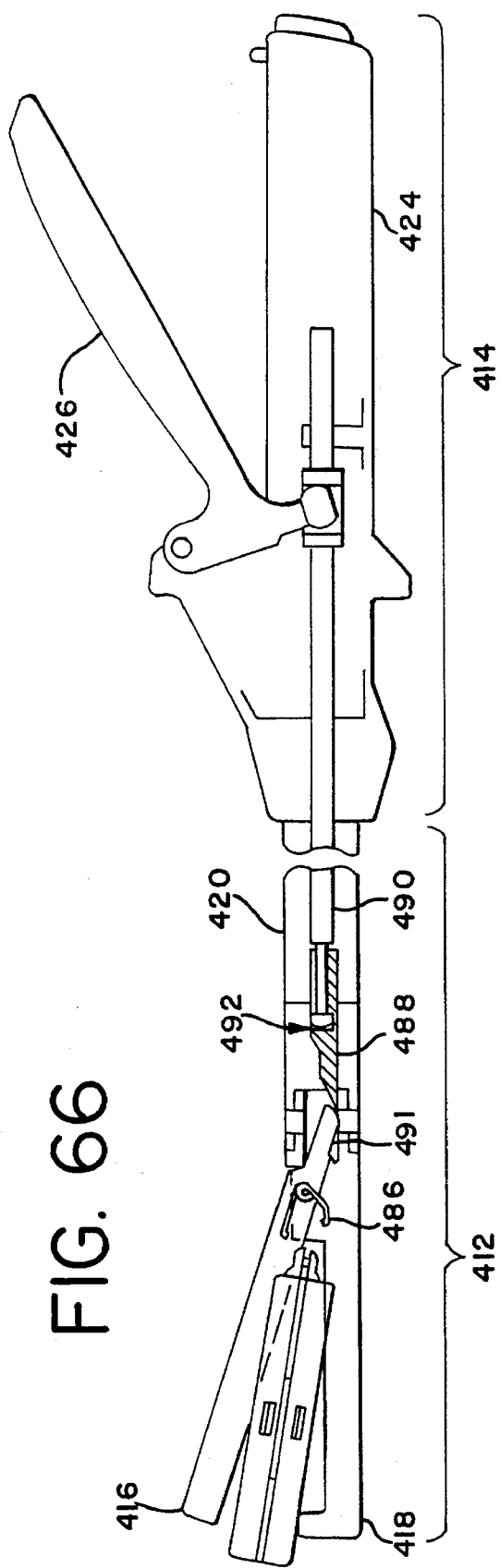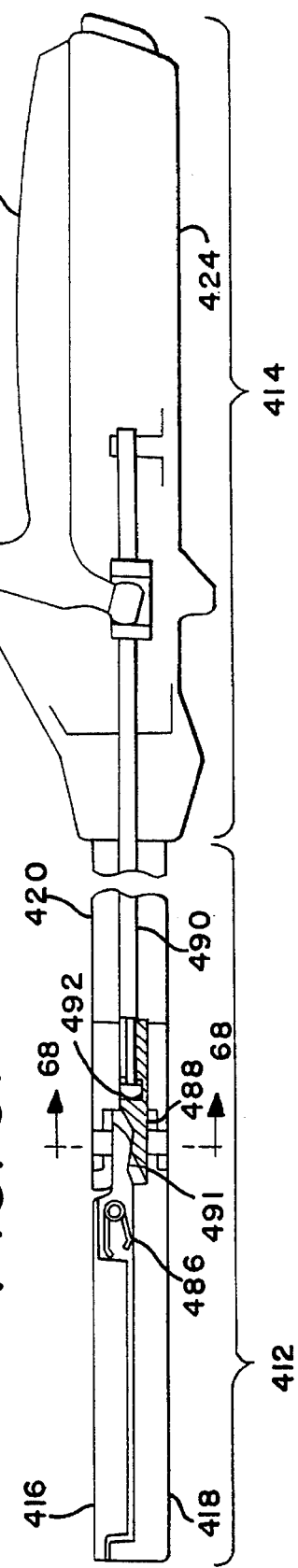

ENDOSCOPIC SURGICAL INSTUMENT AND STAPLES FOR APPLYING PURSE STRING SUTURES

CROSS-REFERENCES TO RELATED APPLICATIONS

This is a continuation-in-part of U.S. patent application Ser. No. 07/881,010, filed May 8, 1992, now U.S. Pat. No. 5,242,457.

BACKGROUND OF THE INVENTION

1. Field of the Invention

The present invention generally relates to a surgical instrument and staples for applying purse string sutures to human tissue and, more particularly, to a surgical instrument and method in which a purse string suture is secured to human tissue by a plurality of staples. In addition, this invention relates to a surgical staple for securing a purse string suture to human tissue in which the staple body is adapted to be slidably attached to the purse string suture.

In an alternative aspect, this invention relates to endoscopic instruments and methods and, more particularly, to an endoscopic surgical instrument and method for applying purse string sutures to body tissue by a plurality of staples.

2. Description of the Prior Art

In the prior art, it is known to use a purse string suture to close a tubular section of tissue, e.g., intestinal tissue, prior to the performance of an end-to-end anastomosis with a circular suturing instrument. The purse string suture is attached to a surgical needle which is used by a surgeon to manually stitch the purse string suture about the periphery of the tubular section of tissue. After the purse string suture is stitched to the tissue, the ends of the purse string suture are pulled to tighten the stitches and draw the tissue together. Then, the purse string suture is wrapped and tightened about the tubular section of tissue. In the manual stitching of the purse string suture, it is difficult to obtain uniform penetration of the purse string suture into the tissue. It is also difficult to obtain stitches which are uniform in length and are evenly spaced apart. As a result, some of the stitches may rip away from the tissue when the ends of the purse string suture are pulled.

Purse string suture devices are known in the prior art which comprise a pair of serrated tissue clamping jaws provided with teeth for clamping the tissue to be sutured therebetween. Such devices include needle passages which extend through the teeth on each jaw for receiving a needle attached to a suture to be threaded through the tissue. In use, the tissue to be sutured is clamped between the jaws and the needle is manually passed through the needle passages in both jaws to thread the suture through the tissue. Thereafter, the jaws are opened and the purse string suture is tightened and wrapped to draw the tissue together. Because the tissue may be gathered unevenly between the jaws, it is sometimes difficult to obtain uniform penetration of the needle and suture into the tissue. Thus, when the ends of the purse string suture are pulled to gather the tissue together, there is a tendency for at least some of the stitches formed by the purse string suture to rip away from the tissue. Also, it is possible that some of the stitches may extend through both walls of the tubular section of tissue with the result that the tissue is not uniformly drawn together when the ends of the purse string suture are pulled to draw the tissue together.

In the prior art, it has been proposed to provide purse string suture devices which utilize a plurality of staples for applying purse string sutures to human tissue. Both anvil carrying devices and anvilless devices have been proposed for applying the staples and the purse string sutures to the tissue.

For example, U.S. Pat. No. 4,749,114 discloses a purse string applicator which includes an anvil carrier with a plurality of anvils for insertion in a tubular section of tissue and a pair of staple cartridges disposed on opposite sides of the anvil carrier. Each cartridge has a row of staples and the purse string suture extends across each row of staples. The applicator includes a pair of pushers each having a plurality of pusher fingers for driving the staples from the cartridges through the tissue against the anvils of the carrier. The staples in each row are deformed and secured to the tissue and the purse string suture is slidably retained between the staples and the tissue.

In addition, U.S. Pat. No. 4,821,939 discloses an anvilless surgical stapler for applying purse string sutures to human tissue. The stapler includes a pair of staple cartridges each having a plurality of openings for receiving a plurality of surgical staples. The cartridges include opposed projections which define grooves at both ends of the cartridges to receive a purse string suture. Each cartridge includes a pair of staple forming lips which define an outlet of lesser width than the openings. Each cartridge includes a plurality of pushers for driving the staples from the openings through the outlets and into the tissue clamped between the cartridges. As the staples are expelled from the openings, the lips deform the staple legs inwardly toward each other to penetrate into and grip the tissue. The purse string suture is located underneath each staple and is thereby attached to the tissue.

In the above examples, the purse string suture is located underneath the staples and is retained against the tissue by the staples. Consequently, when the ends of the purse string suture are pulled by a surgeon to draw the tissue together, there is some resistance to movement of the purse string suture relative to the staples and tissue. Thus, it is possible that some portions of the tissue may not be tightly drawn together by pulling on the ends of the purse string suture.

Accordingly, it is desirable to provide a surgical staple for securing a purse string suture to human tissue which does not clamp the purse string suture against the tissue. Also, it is desirable to provide a surgical staple for securing a purse string suture which presents minimal resistance to the movement of the purse string suture after the staple is secured to the tissue. In addition, it is desirable to provide a surgical staple for securing a purse string suture in which the staple body is slidably attached to the purse string suture.

Further, it is desirable to provide a method for securing a purse string suture to human tissue by a plurality of staples which are slidably attached to the purse string suture and present minimal resistance to the movement of the purse string suture relative to the tissue. Also it is desirable to provide a surgical instrument having a staple cartridge in which the purse string suture can be slidably attached to the surgical staples prior to the operation of the instrument to secure the staples and the purse string suture to the tissue.

Further, it is desirable to provide an endoscopic surgical instrument and method for securing purse string suture by a plurality of staples which are slidably attached to the purse string suture and present minimal resistance to the movement of the purse string suture relative to the tissue. For such endoscopic surgical instrument, it is desirable to provide a staple cartridge containing purse string suture and staples that is insertable into the instrument. Further, it is desirable to provide an endoscopic surgical instrument having a rotatable and/or articulatable endoscopic portion and a knife blade for cutting the tissue after it has been stapled.

SUMMARY OF THE INVENTION

The present invention achieves an improved surgical staple for securing a purse string suture to human tissue. The surgical staple comprises a staple body comprising an elongated strip of deformable material including a pair of legs adapted to be inserted into the tissue, the legs being deformable upon insertion into the tissue to secure the staple body to the tissue, and the staple body including means for slidably attaching the purse string suture to the staple. Preferably, the receiving means comprises an eyelet formed on the staple body through which the purse string suture is threaded. The eyelet can be located on the opposite side of the staple body from the staple legs or on the same side of the staple body as the staple legs.

In a preferred embodiment of the surgical staple, the staple body is formed into a loop to provide an eyelet through which the suture is threaded. The loop is formed on the opposite side of the staple body from the staple legs or on the same side of the staple body as the staple legs.

Another embodiment of the surgical staple comprises a staple body including two or more legs adapted to be inserted into the tissue, the legs including barbed ends for anchoring the legs to the tissue, and the staple body including means for slidably receiving the purse string suture. Preferably, the surgical staple comprises a staple body shaped into a ring to provide an eyelet for receiving a purse string suture and including two or more legs with barbed ends for anchoring the legs to the tissue. In a preferred embodiment of the surgical staple, a plurality of legs extend in a fan-like configuration from the staple body. The legs are bent alternately forward and rearward relative to the ring.

Another aspect of the invention relates to an improved method for securing a purse string suture to a tubular section of tissue. The method comprises the steps of positioning a plurality of staples about the periphery of a tubular section of tissue, slidably attaching a purse string suture to the staples, and driving the staples into the tissue to secure the purse string suture thereto. Preferably, each of the staples includes an eyelet through which the purse string suture is threaded to attach the purse string suture to the staples.

The present invention also achieves an improved surgical instrument for applying purse string sutures to human tissue. The purse string suture instrument comprises a pair of staple cartridges having opposed tissue clamping surfaces for clamping the tissue therebetween. A row of staple receiving slots is formed in each of the cartridges with each slot being adapted to receive a staple with its legs pointing toward the tissue clamping surface of the cartridge. A central slot extends along the tissue clamping surface of each cartridge for receiving a purse string suture connected to the staples in each of the staple receiving slots. A staple pusher bar is slidably mounted in each cartridge and adapted to engage and bend the legs of each staple toward the tissue clamping surface of the cartridge upon movement of the staple pusher bar relative to the cartridge. Actuating means is provided for sliding the pusher bar in each staple cartridge to bend the staple legs and secure the staples and the purse string suture to the tissue clamped between the cartridges.

Preferably, the central slot in each staple cartridge intersects each of the staple receiving slots therein. Also, the staple pusher bar is movable relative to the cartridge in a direction parallel to the row of staples therein. The pusher bar includes a series of opposed pairs of wedge-shaped protrusions corresponding to the staple receiving slots in the cartridge, with each pair of wedge-shaped protrusions being adapted to engage and bend the legs of the staple toward the tissue clamping surface into an overlapped configuration when the staple pusher bar is moved longitudinally relative to the cartridge.

According to another aspect of the invention, a staple cartridge comprises an elongated housing including a tissue engaging surface, a plurality of transverse slots extending into the housing from the tissue engaging surface for receiving staples therein, and an elongated central slot for receiving a purse string suture attached to each of the staples. The elongated central slot extends longitudinally along the housing and intersects the transverse slots. A staple pusher bar is slidably mounted for longitudinal movement in the housing with the staple pusher bar being adapted to engage and bend the legs of each staple toward the tissue clamping surface to secure the staples and the purse string suture to the tissue.

Another aspect of the invention comprises an endoscopic stapler having a pair of jaws. At least one of the jaws is movable between an open position and a closed position. Each jaw contains a staple cartridge for holding a plurality of staples. Each cartridge contains a closer mechanism for closing the staples. The instrument has a handle portion containing a jaw actuator for moving the jaws and a trigger mechanism for actuating the closer mechanism.

Other features of the invention include rotation of the endoscopic portion relative to the handle portion, articulation of the jaws between a straight configuration and an angled configuration, a jaw articulation control on the handle, a cutting blade for cutting tissue adjacent the jaws, and a blade actuator on the handle.

In an alternative aspect of the invention, the staple cartridge is configured to coact with another cartridge of the same design. The staple pusher bar within the cartridge coacts with another staple pusher bar of the same configuration which is located in another cartridge adjacent to the first cartridge. The cartridge has a plurality of staple receiving slots and a central longitudinal slot for permitting passage of a longitudinally extending suture.

An alternative aspect of the invention includes an endoscopic surgical stapler having a stapling portion located at its distal end for applying a plurality of staples in a single application wherein the stapling portion is articulatable between a straight configuration and an angled configuration. An articulation control in the handle variably articulates the stapling portion. A trigger mechanism in the handle actuates the stapling portion.

An alternative aspect of the invention includes a method for applying purse string suture and staples to a body tissue endoscopically. The method includes the steps of providing an elongated surgical instrument with a cartridge containing purse string suture and staples, extending the cartridge through a trocar and into a body cavity adjacent a body tissue, and firing the staples into the body tissue without piercing completely through the body tissue so as to retain the suture on the body tissue.

Alternative steps in the method in accordance with the invention include providing a second cartridge at the distal end of the elongated instrument, providing a set of jaws at the distal end of the instrument, closing the jaws around two layers of body tissue, firing staples from each cartridge wherein each staple pierces one of the layers of tissue without piercing the other of the layers of tissue, articulating the jaws to an angled position after the Jaws are extended through the trocar, rotating the endoscopic portion relative to the handle portion, providing a knife blade adjacent one of the Jaws and cutting the body tissue with the knife blade.

BRIEF DESCRIPTION OF THE DRAWINGS

The foregoing and other objects, aspects and advantages will be better understood from the following detailed description of the preferred embodiments of the invention with reference to the drawings, in which:

FIG. 1 is a side view of a first embodiment of a surgical staple for securing a purse string suture to human tissue;

FIG. 2 is a top view of the surgical staple of FIG. 1;

FIG. 3 shows the surgical staple of FIG. 1 with its legs deformed to attach the staple and a purse string suture to the tissue;

FIG. 4 is a side view of a second embodiment of a surgical staple for securing a purse string suture to human tissue;

FIG. 5 is a bottom view of the surgical staple of FIG. 4;

FIG. 6 shows the surgical staple of FIG. 4 with its legs deformed to attach the staple and a purse string suture to the tissue;

FIG. 7 is a side view of a third embodiment of a surgical staple for securing a purse string suture to human tissue;

FIG. 8 shows the surgical staple of FIG. 7 with its legs deformed to attach the staple and a purse string suture to the tissue;

FIG. 9 is a side view of a fourth embodiment of a surgical staple for securing a purse string suture to human tissue;

FIG. 10 shows the surgical staple of FIG. 6 with its legs deformed to attach the staple and a purse string suture to the tissue;

FIG. 11 is an enlarged view of a modified form of the surgical staple shown in FIG. 1;

FIG. 12 is an enlarged view of another form of the surgical staple shown in FIG. 1;

FIG. 13 is an enlarged view of a modified form of the surgical staple shown in FIG. 4;

FIG. 14 shows a purse string suture secured to a tubular section of tissue by a plurality of staples in accordance with this invention;

FIG. 15 shows a fifth embodiment of a surgical staple for securing a purse string suture to human tissue which includes a plurality of legs provided with barbed ends for anchoring the staple in the tissue;

FIG. 16 is an end view of the surgical staple of FIG. 15;

FIG. 17 shows the surgical staple of FIG. 15 anchored in the tissue with a purse string suture threaded therethrough;

FIG. 18 shows a purse string suture threaded into a plurality of surgical staples of the type shown in FIG. 1;

FIG. 19 shows a purse string suture threaded into a plurality of surgical staples of the type shown in FIG. 4;

FIG. 20 shows a purse string suture threaded into a plurality of surgical staples of the type shown in FIG. 15;

FIG. 21 is a perspective view showing the purse string instrument of the present invention with its jaws open;

FIG. 22 is a side view of the purse string suture instrument with its jaws closed;

FIG. 23 is a bottom view of the purse string suture instrument;

FIG. 24 is an end view of the purse string suture instrument;

FIG. 25 is a partially cutaway plan view of the opposite side of the purse string suture instrument shown in FIG. 22;

FIG. 26 is an enlarged section taken along line 26—26 of FIG. 22;

FIG. 27 is a partially cutaway view of one of the jaws of the instrument;

FIG. 28 is a partially cutaway perspective view of a first embodiment of a staple cartridge for use with the purse string suture instrument;

FIG. 29 is a top view of the tissue clamping surface of the staple cartridge of FIG. 28;

FIG. 30 is a top view of the staple pusher bar used in the staple cartridge of FIG. 28;

FIG. 33 is a partially cutaway perspective view of a second embodiment of a staple cartridge for use with the purse string suture instrument;

FIGS. 34A–D illustrate modifications of the staple pusher bar of the cartridge of FIG. 33;

FIG. 35 is a top view of the tissue clamping surface of the staple cartridge of FIG. 33;

FIG. 36 is a partially cutaway perspective view of a third embodiment of a staple cartridge for use with the staple shown in FIG. 19;

FIG. 37 is a partially cutaway perspective view of a fourth embodiment of a staple cartridge for use with the staple shown in FIG. 19;

FIG. 38 is a side view of a tissue cutting tool used with the purse string instrument of the present invention;

FIG. 39 is a plan view of the tissue cutting tool of FIG. 38;

FIG. 40 is an enlarged section taken along line 40—40 of FIG. 38;

FIG. 41 is an enlarged section taken along line 41—41 of FIG. 38;

FIG. 42 is an enlarged, partially cutaway plan view of another embodiment of the tissue cutting tool;

FIG. 43 is a side view of the tissue cutting tool of FIG. 42;

FIG. 44 is an enlarged section taken along line 44—44 of FIG. 42;

FIG. 45 is a perspective view of an endoscopic surgical instrument in accordance with the invention;

FIG. 46 is a partial perspective view of the distal end portion of the endoscopic surgical instrument shown in FIG. 45 with the jaws in an open position;

FIG. 47 is an elevational view, partially in cross-section, of the endoscopic surgical instrument shown in FIG. 45 with the endoscopic portion rotated 90° relative to the handle portion;

FIG. 48 is an elevational view of the distal end portion of the endoscopic surgical instrument as shown in FIG. 47 with the jaw portion articulated 45°;

FIG. 49 is an elevational view of the endoscopic surgical instrument shown in FIG. 47 with the jaw portion articulated 90°;

FIG. 54 is a perspective view of a portion of the cartridge shown in FIG. 50 with portions broken away to illustrate interior detail;

FIG. 55 is a perspective view of the cartridge as shown in FIG. 54 with staples and a suture inserted therein;

FIG. 56 is a perspective view of the cartridge, staples and suture as shown in FIG. 55 wherein the hooks on the retaining plate are inserted into eyelets of the staples;

FIG. 63 is an exploded perspective view of two cartridges for use in an endoscopic surgical instrument in accordance with the invention with a cartridge holder between them;

FIG. 63A is a partial perspective view of the upper staple pusher bar shown in FIG. 63;

FIG. 63B is a partial perspective view of the lower staple pusher bar shown in FIG. 63;

FIG. 64 is a perspective view of the assembly of the two cartridges and cartridge holder shown in FIG. 63;

FIG. 64A is a partial perspective view of the stapler pusher bars inserted in the cartridges in FIG. 64;

FIG. 66 is an elevational view partially in section of the instrument shown in FIG. 45 with the jaws in an open position and an assembly of two cartridges and a cartridge holder being inserted therebetween;

FIG. 67 is an elevational view of the instrument as shown in FIG. 66 with the jaws closed;

DETAILED DESCRIPTION OF PREFERRED EMBODIMENTS

Figure 31:
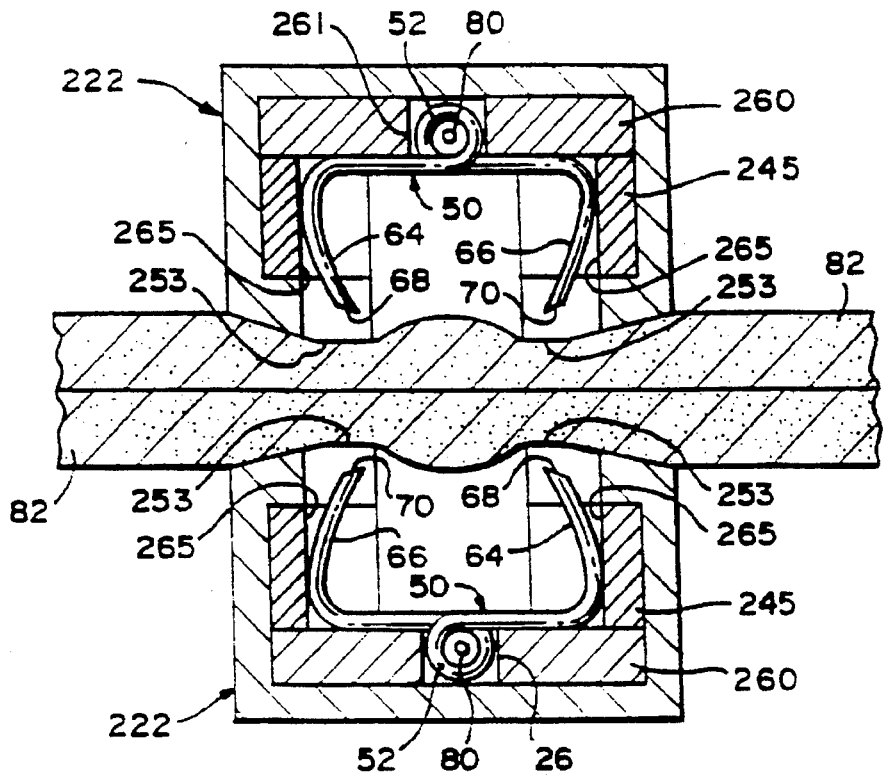
FIG. 31 is a vertical section showing the tissue clamped between a pair of staple cartridges prior to the operation of the staple pusher bars.

Referring to FIG. 1, the present invention is embodied in a surgical staple, generally 50, for securing a purse string suture to human tissue. The staple 50 has a staple body comprising an elongated strip of deformable material which is shaped into a loop 52 at the center of the strip. The loop 52 provides an opening or eyelet 54 for receiving a purse string suture. The staple body also has a pair of arms 56 and 58 which extend substantially horizontally from opposite sides of the loop 52. The arms 56 and 58 have outer portions 60 and 62, respectively, which curve downwardly and provide a pair of depending legs 64 and 66 which are angled inwardly toward each other. The tips 68 and 70 of the legs 64 and 66 are bevelled to provide sharp points which facilitate the insertion of the legs 64 and 66 into human tissue. The loop 52 is formed on the opposite side of the staple body from legs 64 and 66.

As shown in FIG. 3, the surgical staple 50 is particularly useful for securing a purse string suture 80 to a section of human tissue 82, e.g., a tubular section of intestinal tissue. The purse string suture 80 is threaded through the eyelet 54 defined by the loop 52 and is slidably attached to the staple 50. The arms 56 and 58 are deformed by applying pressure to the outer portions 60 and 62 (FIG. 1) to insert the legs 64 and 66 into the tissue 82. When the deformation is completed, the legs 64 and 66 are moved into an overlapping configuration (FIG. 3). Thus, the staple 50 is formed into the configuration of a figure eight including the small upper loop 52 for insertion of the purse string suture 80 and a large lower loop 84 defined by arms 56 and 58 and overlapping legs 64 and 66 for connection to the tissue 82.

Referring to FIG. 4, in a second embodiment of the invention, a surgical staple, generally 90, includes a staple body comprising an elongated strip of deformable material which is shaped into a loop 92 at the center of the strip. The loop 92 provides an opening or eyelet 94 for receiving a purse string suture. The staple body also has a pair of arms 96 and 98 which extend from opposite sides of the loop 92 and which slope slightly downward from the horizontal. The outer portions 100 and 102 of arms 96 and 98 are curved downwardly and provide a pair of legs 104 and 106 which are angled inwardly toward each other. The tips 108 and 110 of legs 104 and 106 are bevelled to provide sharp points which facilitate the insertion of legs 104 and 106 into the tissue. The loop 92 is formed on the same side of the staple body as the legs 104 and 106.

As shown in FIG. 6, the surgical staple 90 is used to secure the purse string suture 80 to the human tissue 82. The purse string suture 80 is inserted into the eyelet 94 defined by the loop 92 and is slidably attached to the staple 90. The arms 96 and 98 are deformed by applying pressure to the outer portions 100 and 102 (FIG. 4) to insert the legs 104 and 106 into the tissue 82. When the deformation is completed, the legs 104 and 106 are moved into an overlapping configuration (FIG. 6). As a result, the staple 90 is deformed into a double-loop configuration with the small upper loop 92 for insertion of the purse string suture 80 which is enclosed by a large lower loop 114 defined by the arms 96 and 98 and legs 104 and 106 for connection to the tissue 82.

Referring to FIG. 7, in a third embodiment of the invention, a surgical staple, generally 120, includes a staple body comprising an elongated strip of deformable material which is shaped into a loop 122 at the center of the strip. The loop 122 provides an opening or eyelet 124 for receiving a purse string suture. The staple body also has a pair of arms 126 and 128 which extend substantially horizontally from opposite sides of the loop 122. The outer portions 130 and 132 of arms 126 and 128 curve downwardly and provide a pair of depending legs 134 and 136 extending perpendicularly downward from arms 126 and 128, respectively. The tips 138 and 140 of the legs 134 and 136 are bevelled to provide sharp points which facilitate the insertion of the legs 134 and 136 into human tissue. The loop 122 is formed on the same side of the staple body as the legs 134 and 136.

As shown in FIG. 8, the surgical staple 120 is used to secure the purse string suture 80 to the human tissue 82. The purse string 80 is inserted into the eyelet 124 defined by the loop 122 and is slidably attached to the staple 120. The arms 126 and 128 are deformed by applying pressure to the outer portions 130 and 132 (FIG. 5) to insert the legs 126 and 128 into the tissue 82. When the deformation is completed, the legs 134 and 136 are moved into an overlapping configuration (FIG. 8). As a result, the staple 120 is deformed into a double-loop configuration with a small upper loop 122 for insertion of the purse string suture 80 which is enclosed by a large lower loop 144 for connection to the tissue 82.

Referring to FIG. 9, in a fourth embodiment of the invention, a surgical staple, generally 150, includes a staple body comprising an elongated strip of deformable material which is shaped into a loop 152 at the center of the strip. The loop 152 provides an opening or eyelet 154 for receiving a purse string suture. The staple body also has a pair of arms 156 and 158 extending from opposite sides of the loop 152 which are each curved in a semi-circular configuration. The arms 156 and 158 terminate in a pair of depending legs 160 and 162, respectively, which point downwardly from the staple body and toward each other. The tips 164 and 166 of legs 160 and 162 are bevelled to provide sharp points to facilitate the insertion of the legs 160 and 162 into the tissue.

As shown in FIG. 10, the surgical staple 150 is used to secure the purse string suture 80 to the human tissue 82. The purse string suture 80 is inserted into the eyelet 154 defined by the loop 152 and is slidably attached to the staple 150. The arms 156 and 158 are deformed by applying pressure to the outer portions thereof to insert the legs 160 and 162 into the tissue 82. When the deformation is completed, the legs 160 and 162 are moved into an overlapping configuration (FIG. 10). Thus, the staple 150 tends to assume the configuration of a figure eight including the small upper loop 152 for insertion of the purse string suture 80 and a large lower loop 168 defined by arms 156 and 158 and overlapping legs 160 and 162 for connection to the tissue 82.

In the embodiments of FIGS. 1, 4, 7 and 9, the body of the surgical staple 50 comprises an elongated strip of deformable material such as stainless steel. Preferably, the strip has a round cross section with a diameter in the range of 0.3 to 0.5 millimeters.

Referring to FIG. 11, in a modified form of the first embodiment, the outer portions 60 and 62 of arms 56 and 58 are curved in a semi-circular shape to provide the legs 64 and 66. The staple 50 consists of an elongated strip of stainless steel having a round cross section with a diameter of 0.3 mm. The loop 52 is round and its inner diameter, i.e., the diameter of eyelet 54 is 0.7 mm. The staple 50 has a width of 5 mm, a height (without the loop 52) of 2.5 mm, and an overall height (including the loop 52) of 3.5 mm.

Referring to FIG. 12, in another form of the first embodiment, staple 50 includes a loop 52 which is generally triangular in shape. The width of eyelet 54 is 1 mm. The staple 50 consists of an elongated strip of stainless steel having a round cross section with a diameter of 0.3 mm. The staple 50 has a width of 5 mm, a height (without the loop 52) of 2.5 mm, and an overall height (including the loop 52) of 3.5 mm.

Referring to FIG. 13, in an example of the second embodiment, the staple 90 consists of an elongated strip of stainless steel having a round cross section with a diameter of 0.3 mm. The diameter of eyelet 94 defined by loop 92 is 0.8 mm. The staple 90 has an overall width of 5 mm and an overall height of 2.5 mm.

Referring to FIG. 15, in a fifth embodiment of the invention, a surgical staple, generally 170, comprises a staple body in the form of a ring 172 which provides a circular eyelet 174 for receiving a purse string suture. The staple body includes a plurality of legs 176 extending downward in a fan-like configuration from the ring 172. Each leg 176 includes a barb 178 formed adjacent to its lower end for anchoring the leg in human tissue.

As shown in FIGS. 15 and 16, the centermost leg 176 is located in the same vertical plane as ring 172. The other legs 176 are bent alternately forward and rearward relative to the ring 172 and the centermost leg 176. The barbs 178 on the bent legs 176 face outwardly away from the vertical plane of the ring 172.

As shown in FIG. 17, the surgical staple 170 is used to secure the purse string suture 80 to the human tissue 82. The purse string suture 80 is inserted into the eyelet 174 defined by the loop 172 and is slidably attached to the staple 170. Then, the surgical staple 170 is driven into the tissue 82 so that the legs 176 are driven below the surface of the tissue 82 while the ring 172 remains above the surface of the tissue 82. The barbs 178 anchor the legs 176 in the tissue with the ring 172 holding the purse string suture 80 at the surface of the tissue 82.

Referring to FIG. 14, in the method of the present invention, a plurality of surgical staples of the type disclosed herein are used to secure the purse string suture 80 to a tubular section of tissue 82. Although a plurality of staples 50 is shown, it is understood that any of the above staple embodiments can be used.

In accordance with the method, a plurality of staples 50 are positioned about the periphery of the tubular section of tissue 82. The purse string suture 80 is attached to the staples by threading the purse string suture 80 through the eyelets 54 provided in the staples 50. Then, the staples 50 are driven into the tissue 82 to secure the purse string 80 thereto.

After the purse string suture 80 is secured to the tubular section of tissue 82, the opposite ends of the purse string suture 80 are pulled to draw the tissue together. The eyelets 54 of the staples 50 slidably support the purse string suture above the tissue 82 so that the staples 50 offer minimal resistance to movement of the purse string suture 80 when its ends are pulled. To complete the procedure, the purse string suture 80 is tightened and wrapped about the tubular section of tissue 82.

As shown in FIG. 18, a plurality of staples 50 of the type shown in FIG. 1 can be used to secure the purse string suture 80 to the tubular section of tissue 82. The purse string suture 80 is threaded through the loops 52 of the staples 50 and is slidably received therein. With the staples 50 positioned about the periphery of the tubular section of tissue 82, the staples 50 are deformed to bend the staple legs 64 and 66 into an overlapping configuration (FIG. 3) to form the loop 84 extending into the tissue 82 to secure the purse string suture 80 thereto.

Similarly, as shown in FIG. 19, a plurality of staples 90 of the type shown in FIG. 4 can be used to secure the purse string suture 80 to the tubular section of tissue 82. The purse string suture 80 is threaded through the loops 92 of the staples 90 and is slidably received therein. With the staples 90 positioned about the periphery of the tubular section of tissue 82, the staples 90 are deformed to bend the staple legs 104 and 106 into an overlapping configuration (FIG. 6) to form the loop 114 extending into the tissue 82 to secure the purse string 80 thereto.

Further, as shown in FIG. 20, a plurality of staples 170 of the type shown in FIG. 15 can be used to secure the purse string suture 80 to the tubular section of tissue 82. The purse string suture 80 is threaded through the eyelets formed in the staples 170 and is slidably received therein. When the staples 170 are positioned about the periphery of the tubular section of tissue 82, the staples 170 are driven into the tissue 82 to secure the purse string suture thereto. The barbed ends of legs 176 anchor the staples 170 to the tissue.

Referring to FIGS. 21 and 22, the invention is embodied in a surgical stapling instrument 200 for applying purse string sutures to human tissue. The surgical instrument 200 comprises a pair of elongated handles 201 and 202 pivotally connected by a pivot pin 203 in a scissors-like arrangement. A pair of finger grips or rings 204 and 205 is provided at the rear of handles 201 and 202, respectively, to facilitate the handling and operation of the surgical instrument 200 by a surgeon. The handles 201 and 202 are provided with latch arms 206 and 207 which project inwardly from the finger grips 204 and 205, respectively. The latch arms 206 and 207 are adapted to interlock when the handles 201 and 202 are pivoted together to a closed position. A finger rest 208 projects rearwardly from the bottom of finger grip 204.

As shown in FIGS. 22 and 23, the handles 201 and 202 include front portions 209 and 210 which support a pair of tissue clamping jaws 211 and 212, respectively. Preferably, the jaws 211 and 212 project perpendicularly from the front handle portions 209 and 210. As shown in FIG. 24, the jaws 211 and 212 have flat, outer surfaces 213 and 214, respectively, which are tapered inwardly toward the outer tips of the jaws. Also, the jaws 211 and 212 have flat, inner surfaces 215 and 216, respectively, which are oriented at a slight angle with respect to each other. As a result, when the handles 201 and 202 are closed to bring the tips of jaws 211 and 212 together, the rear portions of the surfaces 215 and 216 are separated by a distance d which provides a small amount of play in the movement of handles 201 and 202 to bring the jaws 207 and 208 to a fully closed position.

As shown in FIGS. 21 and 22, the outer tip of jaw 211 includes a pair of tabs 217 which are received by side notches 218 formed at the tip of jaw 212. The tabs 217 maintain the jaws 211 and 212 in alignment when the handles 201 and 202 are closed. In addition, a flat tab 219 depends from the upper arm 209 at a point adjacent to the rear of the jaw 211. The depending tab 219 overlaps a flat surface 220 on the lower arm 210 when the handles 201 and 202 are closed.

As shown in FIG. 22, the jaws 211 and 212 support a pair of elongated staple cartridges 222 for receiving the surgical staples and the purse string sutures to be applied to the tissue. Each staple cartridge 222 includes a plurality of transverse slots 224 spaced uniformly apart along the cartridge 222 for receiving the staples to be attached to the tissue. Also, each of the staple cartridges 222 includes a staple forming mechanism, explained in more detail below, for driving the staples into the tissue clamped between the jaws 211 and 212 to attach the purse string suture to the tissue.

Referring to FIGS. 21 and 22, the purse string suture instrument 200 includes a staple actuating lever 225 pivotally mounted by a pivot pin 226 on the handle 201. The lever 225 is bifurcated at its front end to provide a slot 228 (FIG. 21) which allows the latch arm 206 to project upwardly through the lever 225. The latch arm 206 includes a rearwardly extending shoulder 228 which serves as a stop to limit the upward movement of the lever 225. An upright, bifurcated arm 229 is provided at the front of the lever 225 and is connected to an elongated flexible wire 230. As shown in FIG. 25, the front end of wire 230 is formed into an elongated loop 232 which is slidably attached to the back of handle 201 by a screw 233. The front end of the loop 232 is attached to a pair of wires 234 which, in turn, are attached to a pair of pivot arms 236 for actuating the staple forming mechanisms of the cartridges 222 when the lever 225 is operated.

As shown in FIGS. 21 and 22, a locking disc 238 is pivotally mounted on a flange 239 which extends rearwardly from the finger grip 204. The locking disc 238 is pivotable between an upper position (FIG. 22) in which the lever 225 is engaged by the disc 238 and locked against the shoulder 228 and a lower position (FIG. 21) in which the disc 238 engages the finger rest 208 and the lever 225 is disengaged and unlocked for pivotal movement.

As shown in FIG. 27, the pivot arm 236 is pivotally mounted on the front handle portion 209 by a screw 242. The pivot arm 236 includes an upright finger 243 which is slidably received in a transverse slot 244 formed in a staple pusher bar 240 which is slidable longitudinally relative to the staple cartridge 222. The front end of the wire 234 is bent at a right angle and received in a slot 245 formed in the pivot arm 236. A curved spring 246 has its front end received in the slot 245 and its rear end anchored in a hole 247 formed in the front handle portion 209. The spring 246 includes a front portion 248 which curves in a clockwise direction around the screw 242 and a rear portion 249 which curves in a counterclockwise direction about a mounting screw 250. The spring 246 is arranged to normally bias the pivot arm 236 in a clockwise direction about the screw 242 so that the staple pusher bar 240 is biased into the staple cartridge 222. When the wire 234 is pulled rearwardly, the pivot arm 236 is pivoted in a counterclockwise direction against the bias of the spring 236 to slide the staple pusher bar 240 outward relative to the staple cartridge 222. As explained below, this sliding motion of the staple pusher bar 240 causes the staples to be deformed and secured to the tissue clamped between the jaws 211 and 212.

Referring to FIG. 28, a first embodiment of the staple cartridge 222 is adapted for use with the staple 50 (FIG. 1). The staple cartridge 222 comprises an elongated rectangular housing 251 including a pair of side walls 252 which slidably receive the staple pusher bar 240 therebetween. The staple cartridge 251 includes a plurality of transverse staple receiving slots 224 which extend vertically downward into the housing 251. As shown in FIG. 29, each staple receiving slot 224 is located between a pair of ridges 253 which extend upwardly from the top of the housing 251. Each pair of ridges 253 is separated by a valley or depression 254 from the next adjacent pair of ridges 253. The staple cartridge housing 251 is sloped upwardly and inwardly at its outer edges to define sloped surfaces 255 which terminate at the top of the ridges 253. An elongated vertical slot 256 extends longitudinally along the center of the housing 251. The tops of the ridges 253 provide flat tissue clamping surfaces.

The staple receiving slots 224 (FIG. 28) extend downwardly from the tissue clamping ridges 253 and intersect the central vertical slot 256. Each slot 224 is defined by a front wall 257, a rear wall 258 and a pair of end walls 259 which extend vertically downward into the housing 251. The staple 50 is inserted into the slot 254 with its legs 64 and 66 pointing upward toward the tissue clamping ridges 253. A plate 260 is secured inside the housing 251 beneath the pusher bar 240 and provides a ledge for supporting the arms 56 and 58 of the staple 50. The plate 260 includes a slot 261 aligned with each staple receiving slot 224 for receiving the loop 52 of the staple 50.

The staple pusher bar 240 (FIG. 30) consists of a generally rectangular plate provided with a series of opposed pairs of wedge-shaped protrusions 262 extending inwardly from its opposite sides. Each wedge-shaped protrusion 262 defines a flat upright surface 263 which is aligned with the rear wall 258 (FIG. 28) of the slot 224 and a staple forming edge 264 which is slanted inwardly toward the center of the pusher bar 240. The wedge-shaped protrusions 262 are oriented such that the clearance between the opposed staple forming edges 264 decreases as the pusher bar 240 is advanced in the direction of arrow A. Each opposed pair of staple forming edges 264 provides a first set of vertical surfaces 265 which are widely spaced apart and a second set of vertical surfaces 266 which are narrowly spaced apart. The staple 50 inserted in each slot 224 is located adjacent to the front wall 263 of the pusher bar 240. The purse string suture 80 is threaded through the loop 52 of the staple 50 in each slot 224.

Figure 32:
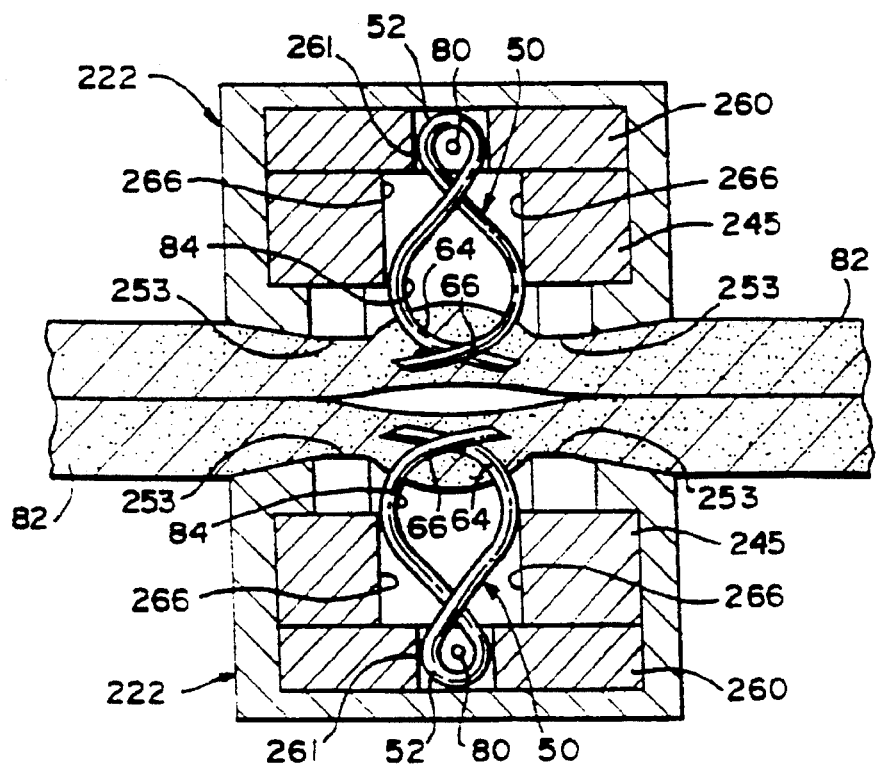
FIG. 32 is a vertical section showing the tissue clamped between a pair of staple cartridges after the operation of the staple pusher bars.

As shown in FIG. 31, the tissue 82 is clamped between the pair of staple cartridges 222 prior to the actuation of the staple pusher bars 240. The staple legs 64 and 66 are located between the surfaces 265 of the pusher bar 240. When the pusher bar 240 is advanced in the direction of arrow A (FIG. 30), the slanted edges 264 engage and bend the staple legs 64 and 66 toward each other. As shown in FIG. 32, the tips 68 and 70 of the staple legs 64 and 66 are guided into the tissue 82 between the ridges 253 of the staple cartridge 222. When the pusher bar 240 is fully advanced, the staple legs 64 and 66 are located between the surfaces 266 of the staple pusher bar 240. As a result, each staple 50 is deformed into the configuration of a figure eight with the staple legs 64 and 66 overlapped to form the loop 84 to secure the staple 50 and the purse string suture 80 to the tissue 82.

Referring to FIG. 33, in an alternative embodiment, a staple cartridge 270 comprises an elongated rectangular housing 271 including a pair of side walls 272 which slidably receive a staple pusher bar 273 therebetween. The staple cartridge 270 includes a plurality of transverse staple receiving slots 274 which extend vertically downward into the housing 271. Each staple receiving slot 274 is located between a pair of ridges 275 which extend upwardly from the top of the housing 271. Each pair of ridges 275 is separated by a valley or depression 276 from the next adjacent pair of ridges 275. The staple cartridge housing 271 is sloped upwardly and inwardly at its outer edges to define sloped surfaces 277 which terminate at the top of the ridges 275. An elongated vertical slot 278 extends longitudinally along the center of the housing 271. The top of the vertical slot 275 opens into a longitudinal V-shaped groove defined by inclined surfaces 279 which are sloped upwardly and outwardly from the vertical slot 278 and terminate at the top of ridges 275. The tops of the ridges 275 provide flat tissue clamping surfaces.

The staple receiving slots 274 extend downwardly from the tissue clamping ridges 275 and intersect the central vertical slot 278. Each slot 274 is defined by a front wall 280, a rear wall 281 and a pair of end walls 282 which extend vertically downward into the housing 271. The staple 50 is inserted into the slot 274 with its legs 64 and 66 pointing upward toward the tissue clamping ridges 275. A plate 283 is secured inside the housing 271 beneath the pusher bar 273 and provides a ledge for supporting the arms 56 and 58 of the staple 50. The plate 283 includes a notch 284 aligned with each staple receiving slot 274 for receiving the loop 52 of the staple 50.

Referring to FIGS. 33 and 35, in a preferred embodiment of the staple cartridge 270, each staple receiving slot 274 includes a recess 285 formed in its front wall 280. The purpose of the recess 285 is to enlarge the staple receiving slot 274 allow the legs 64 and 66 of the staple 50 to be bent into an overlapping configuration.

In the embodiment of FIG. 33, the staple pusher bar 273 includes a series of opposed pairs of wedge-shaped protrusions 286 extending inwardly from its opposite sides. Each wedge-shaped protrusion 286 defines a flat upright surface 287 aligned with the rear wall 281 of the slot 254. Also, each wedge-shaped protrusion 286 defines a staple forming edge 288 which is slanted inwardly toward the center of the pusher bar 273. In this embodiment, a V-shaped staple forming channel extends along the edge 288 of each wedge-shaped protrusion 286.

A staple 50 is inserted into each slot 274 with its legs 64 and 66 located adjacent to the front walls 281 of the pusher bar 273. The purse string suture 80 is threaded through the loop 52 of the staple 50 in each slot 274. When the pusher bar 273 is advanced in the direction of arrow A, the slanted edges 88 engage the staple legs 64 and 66 and bend the legs 64 and 66 toward each other. As a result, the tips 68 and 70 of the staple legs 64 and 66 are guided into the tissue 82 above the ridges 275 of the staple cartridge 270. When the pusher bar 273 is fully advanced, the staple 50 is deformed into the configuration of a figure eight with the staple legs 64 and 66 overlapped into the loop 84 (FIG. 3) to secure the staple 50 and the purse string suture 80 to the tissue 82.

FIGS. 34A–D illustrate examples of the configurations which can be used for the staple forming edge 288 of the staple pusher bar 273. In FIG. 34A, the protrusion 286 has a staple forming edge 288 consisting of an upright, vertically oriented surface 290. In FIG. 34B, the staple forming edge 288 includes sloped surfaces 291 and 292 which intersect at an elongated apex line 293 to define a V-shaped staple forming channel. The surfaces 291 and 292 are equal in size and are sloped at equal and opposite angles to the vertical. In FIG. 34C, the staple forming edge 288 has a V-shaped channel consisting of sloped surfaces 294 and 295 which are eloped at different angles and intersect at an elongated apex line 296 closer to the bottom of the staple pusher bar 273. In FIG. 34D, the staple forming edge 288 consists of a flat surface 297 which is sloped upwardly and outwardly at an angle a of approximately 10° from the vertical.

As shown in FIG. 36, another embodiment of the staple cartridge 222 includes a modified staple pusher bar 300 for use with a staple 50 (FIG. 19) in which the loop 52 is triangular in shape. The staple pusher bar 300 includes a series of opposed pairs of wedge-shaped protrusions 302 extending inwardly from its opposite sides. Each wedge-shaped protrusion 302 defines a flat upright surface 303 which is aligned with the rear wall 258 of the slot 224 and a staple forming edge 304 which is slanted toward the center of the pusher bar 301. The staple forming edges 304 provide a first set of vertical surfaces 305 which are widely spaced apart and a second set of vertical surfaces 306 which are narrowly spaced apart. On each side of the staple pusher bar 301, a ledge 307 projects inwardly toward the center of the pusher bar 301. Each ledge 307 is provided with an elongated bevelled edge 308 which allows the ledge 307 to move past the triangularly shaped loop 52 of the staple 50 when the staple pusher bar 300 is actuated. A pair of opposed notches 309 is formed in the ledges 307 to receive the arms 56 and 58 of the staple 50.

As shown in FIG. 37, another embodiment of the staple cartridge 270 includes a modified staple pusher bar 310 for use with a staple 50 (FIG. 19) in which the loop 52 is triangular in shape. The staple pusher bar 310 includes a plurality of pairs of wedge-shaped ramps each including an upwardly inclined surface 312 and an inwardly slanted surface 313 for deforming the legs 64 and 66 of the staple 50 when the pusher bar 310 is actuated. On each side of the staple pusher bar 310, a ledge 317 projects inwardly toward the center of the pusher bar 310. Each ledge 317 is provided with an elongated bevelled edge 318 which allows the ledge 317 to move past the triangularly shaped loop 52 of the staple 50 when the staple pusher bar 310 is actuated. A pair of opposed notches 319 is formed in the ledges 317 to receive the arms 56 and 58 of each staple 50.

Referring to FIG. 38, a tissue cutting tool or knife 320 includes an elongated handle 321 provided with a finger loop 322 at one end of the handle 321 to facilitate use of the knife 320 by a surgeon. The other end of handle 321 is attached to an extension rod 323 which, in turn, is attached to a knife head 324 which supports a cutting blade 325. The knife head 324 includes the curved slot 326 (FIG. 40) which extends across a front portion of the head 324. The cutting blade 325 is force fit into the slot 326 and projects outwardly and forwardly from one side of the head 324. The extension rod 323 includes an axially extending shaft 327 (FIG. 38) which is received in an axial bore formed in the handle 321. The shaft 327 is secured to the handle 321 by a transverse retainer screw 328. The knife head 324 includes an axially extending shaft 329 received in an axial bore formed in the extension rod 323 and secured by a retainer screw 330 to the extension rod 323. As shown in FIG. 41, the shaft 327 is notched to receive the retainer screw 328. Also, the shaft 329 is notched to receive the retainer screw 330. Referring to FIG. 42, in an alternative embodiment to the tissue cutting tool, a knife head 332 which is detachably connected to the extension rod 323. The knife head 332 includes an axially extending shaft 333 (FIG. 43) which is received in an axial bore formed in the extension rod 323 and is secured by the retainer screw 330. The shaft 333 includes one or more notches 334 for receiving the retainer screw 330. The knife head 332 includes a removable support 335 which supports a knife blade 336 extending outwardly and forwardly from one side of the knife head 332. The knife support 335 includes a pair of flexible arms 337 provided with hooked ends 338 which are captured by a pair of notches 339 formed in the knife head 332. Also, a screw 340 (FIG. 44) is threaded into an axial bore 340 in the knife head 332 to secure the knife support 335 and the knife blade 336 to the knife head 332. A protective bracket 341 (FIG. 42) is pivotally attached to the knife head 332 by a pair of screws 342. The bracket 341 includes a pair of flanges 343 which normally cover the notches 339 when the knife support 335 is attached to the knife head 332.

To allow replacement of the knife support 335 and knife blade 336, the screws 342 are loosened and the bracket 341 is pivoted away from the knife head 332 to expose the notches 339. As a result, the knife support 335 can be detached from the knife head 332. After another knife support 335 is fitted on the knife head 332, the bracket 341 is pivoted inwardly and the screws 342 are tightened to secure the bracket 341 over the notches 339.

In the operation of the purse string suture instrument 200, a plurality of staples 50 are inserted into the staple receiving slots 224 of both staple cartridges 222. Each staple 50 is oriented with its loop 52 received in the notch 261 at the bottom of the staple receiving slot 224 and with its legs 64 and 66 pointing upwardly toward the tissue clamping ridges 253. A single purse string suture 80 is threaded through the loops 52 of all staples 50 in both staple cartridges 222.

After the staples 50 and the purse string suture 80 are loaded into the staple cartridges 222, the jaws 211 and 212 are opened by grasping finger grips 204 and 205 and moving the handles 201 and 202 apart. The instrument 200 is positioned with its opened jaws 211 and 212 on opposite sides of a tubular section of tissue 82. Then, the jaws 211 and 212 are closed by grasping the finger grips 204 and 205 and moving handles 201 and 202 together to clamp the tissue 82 between the cartridges 222 on the jaws 211 and 212. The handles 201 and 202 are latched together by the latch arms 206 and 207 to hold the jaws 211 and 212 closed.

As shown in FIG. 31, the tissue 82 is pinched between the opposed tissue clamping ridges 253 and urged into a slight bulge at the center of each staple cartridge 222. Initially, prior to the actuation of the staple pusher bar 240, the widely spaced vertical surfaces 265 of the pusher bar 240 are located adjacent to the staple legs 64 and 66.

Referring to FIGS. 21 and 22, the staple actuating lever 225 is unlocked by pivoting the locking disc 238 from its upper locked position to its lower unlocked position (shown in phantom lines) engaging finger rest 208. Then, the staple actuating lever 225 is depressed to pivot arm 229 in a clockwise direction about pivot pin 226 and to pull the flexible wire 230 rearwardly. As a result, the connecting wires 234 are pulled rearwardly and each pivot arm 236 (FIG. 27) is pivoted about its pivot screw 242 against the bias of spring 248. The pivotal movement of each pivot arm 236 is transmitted via the pin 243 and slot 244 into longitudinal movement of the staple pusher bar 240 in the direction of arrow A relative to the staple cartridge 222.

Referring to FIG. 28, when the pusher bar 240 is moved in the direction of arrow A, the slanted staple forming edges 264 engage and bend the staple legs 64 and 66 toward each other. As shown in FIG. 32, the tips 68 and 70 of the staple legs 64 and 66 are guided into the tissue 82 between the ridges 253 of the staple cartridge 222. When the pusher bar 240 is fully advanced, the staple legs 64 and 66 are located between the narrowly spaced vertical surfaces 266 of the staple pusher bar 245. Each staple 50 is deformed into the configuration of a figure eight with the staple legs 64 and 66 overlapped to form the loop 84 to secure the staple 50 and the purse string suture 80 to the tissue 82.

When the staple actuating lever 225 is depressed, the staple pusher bars 240 in both staple cartridges are simultaneously actuated. As a result, all of the staples 50 in both cartridges 222 are simultaneously bent to secure the purse string suture 80 to the tissue.

Next, prior to the opening of jaws 211 and 212, the tubular section of tissue 82 is cut crosswise in front of the jaws 211 and 212 by using the knife 320 (FIG. 38). The knife 320 is positioned with its cutting blade 335 adjacent to the front of the purse string suture instrument 200. Then, using the front edges of the jaws 211 and 212 as a guide, the cutting blade 335 is drawn across the front of the purse string suture instrument 200 to cut the tubular section of tissue in the crosswise direction. After the tissue is cut, the handles 201 and 202 are unlatched and moved apart to separate the jaws 211 and 212 and unclamp the tissue. As shown in FIG. 14, the purse string suture 80 remains attached to the tubular section of tissue 82 by a plurality of staples 50. Thereafter, both ends of the purse string suture 80 are pulled to close the tubular section of tissue 82 and the purse string suture 80 is tightened and wrapped about the tubular section of tissue 82. The loops 52 of the staples 50 allow the purse string suture 80 to be moved easily through the staples 50 with minimal resistance or interference from the tissue 82.

Preferably, the purse string suture instrument 200 is a reusable tool constructed of stainless steel. The staple cartridges 222 are one-shot disposable units which are detachable from the jaws 211 and 212 of the instrument. Also, the tissue cutting tool 320 is constructed of stainless steel.

In another aspect in accordance with the invention, there is provided a purse string suture stapler for endoscopic use. Referring to FIG. 45, the suture stapler 410 includes a rotatable endoscopic portion 412 and a handle portion 414. The endoscopic portion 412 includes a jaw portion 415 having a pair of articulating jaws 416 and 418, an outer tube 420 and a rotation knob 422, as described in detail below. The handle portion 414 includes a handle 424, a lever 426 for opening and closing the jaws, a latch 430, a safety lock button 432, a jaw articulation crank 434, a staple firing trigger 436, and a blade actuator 438, as described in detail below.

Referring to FIGS. 45 and 46, the jaws 416 and 418 are movable between an open position (FIG. 46) and a closed position (FIG. 45). Preferably, one jaw 416 is movable and the other jaw 418 is stationary. Each jaw contains a staple cartridge 440 as described in detail below.

Referring to FIGS. 47-49, the jaw portion 415 is articulatable as a unit between a position that is parallel to the outer tube (FIG. 47) and angled positions (FIGS. 48 and 49). Preferably, the jaws may be variably angled between a parallel orientation (FIG. 47) and a 90° orientation (FIG. 49) by movement of the articulation crank 434.

As seen in FIGS. 45 and 47, the endoscopic portion 412 is rotatable relative to the handle portion 414. In FIG. 47, the endoscopic portion 412 has been rotated 90° so that the jaw portion 415 articulates in a downward direction rather than a lateral direction relative to the handle portion 414.

The rotation of the endoscopic portion 412 relative to the handle portion 414 is effected by a rotatable connection between the outer tube 420 and the handle 424. A rotation knob 422 is connected to the proximal end of the outer tube 420.

Figure 50:
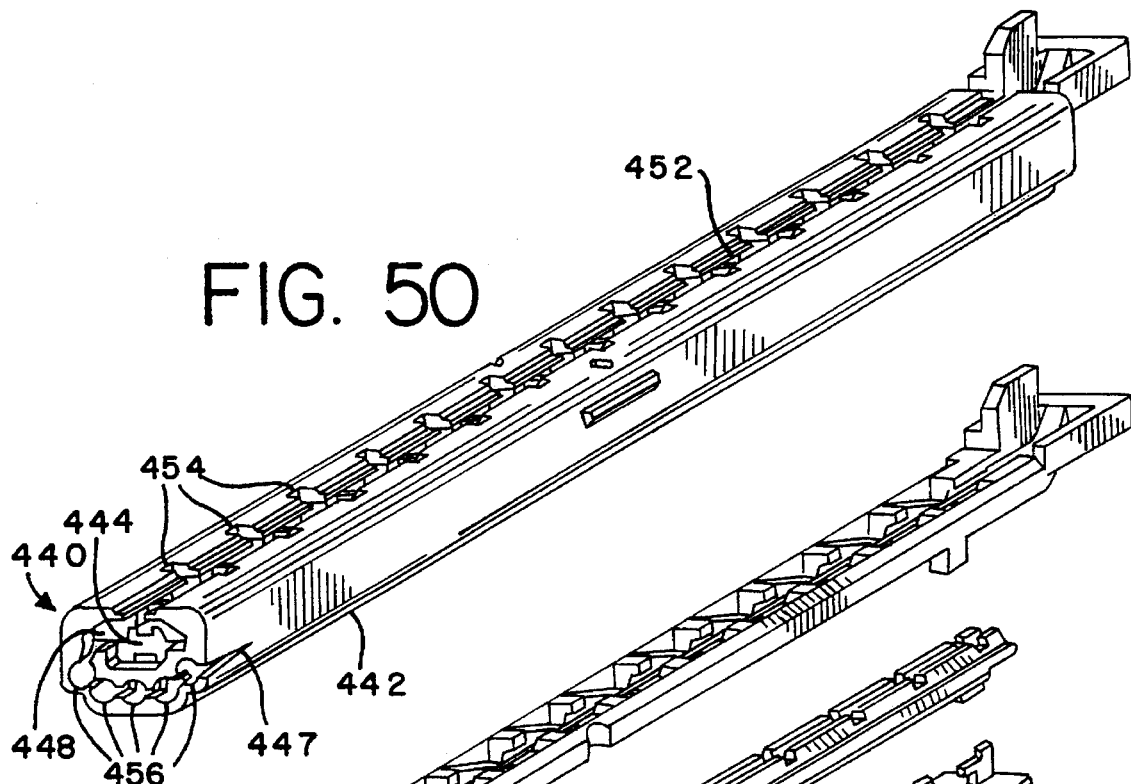
FIG. 50 is a perspective view of a cartridge for use in an endoscopic surgical instrument in accordance with the invention.
Figure 51:
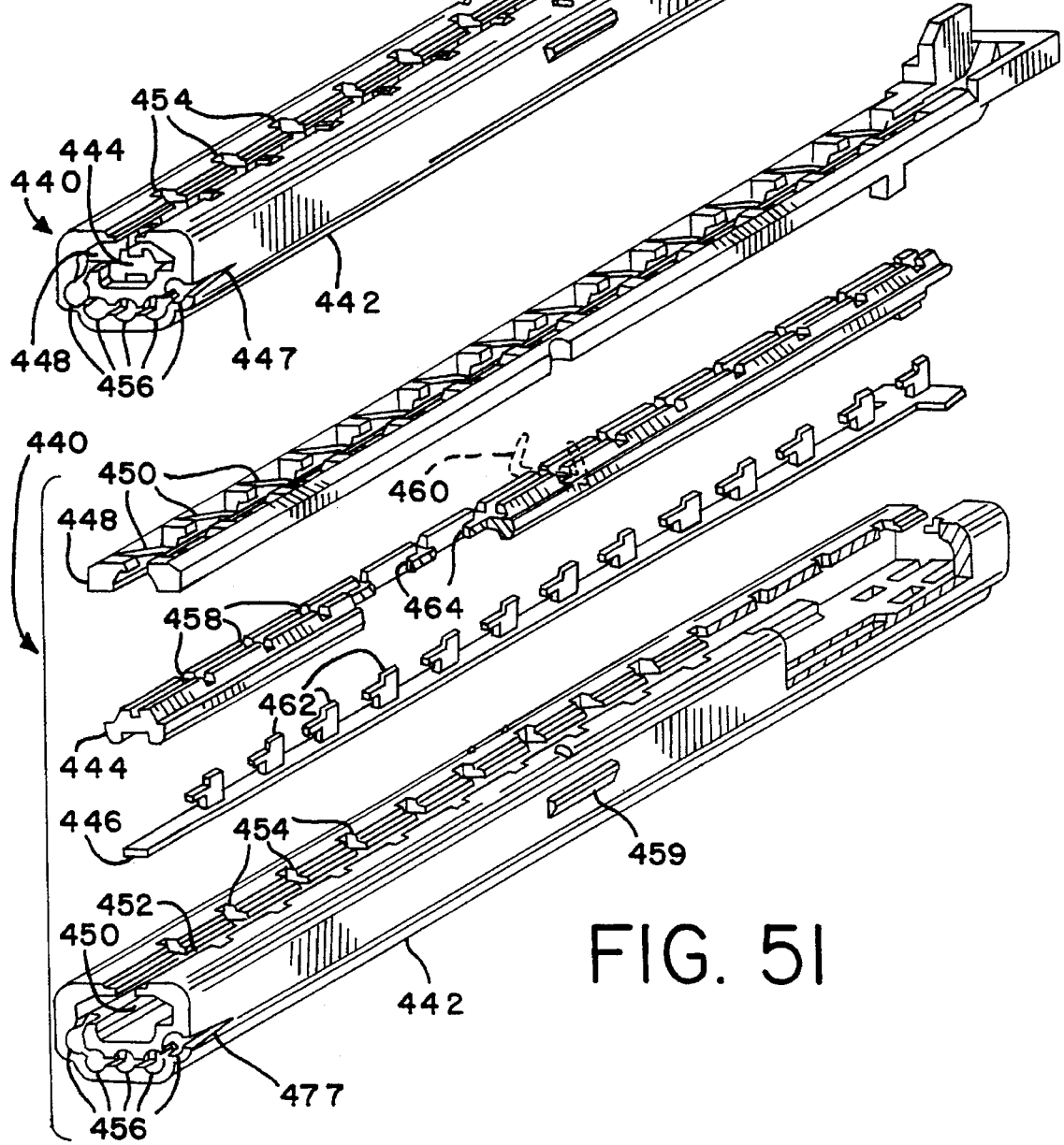
FIG. 51 is an exploded view of the cartridge shown in FIG. 50 wherein a portion of the staple base is broken away to illustrate interior detail.

Referring to FIGS. 50 and 51, each staple cartridge 440 includes a cartridge housing 442, a staple base 444, a retainer plate 446 (FIG. 51), and a staple pusher bar 448. Referring to FIG. 51, the cartridge housing 442 defines an interior space 450 for housing the staple base 444, retainer plate 446 and staple pusher bar 448. The cartridge housing 442 defines a central longitudinal slot 452 for allowing passage of longitudinally-extending suture, and further defines a plurality of transverse, staple receiving slots 454 for allowing passage of staples as described herein.

The cartridge housing 442 (FIG. 51) defines a plurality of longitudinally extending wells 456 for releasably containing a plurality of loops of an extended length of suture, as discussed further below. A catch 459 on the side of the cartridge housing engages a corresponding lip 486 (see FIG. 65) in the jaw for securing the cartridge in the jaw.

The staple base 444 (FIG. 51) defines a plurality of transverse notches 458 for receiving and supporting staples. Each notch 458 holds a staple as shown by the staple 460 indicated by phantom lines.

The retainer plate 446 (FIG. 51) includes a plurality of upright hooks 462. The retainer plate 446 is located under the staple base 444. The hooks 462 extend upwardly through hook-receiving slots 464 in the staple base 444. The slots 464 are slightly extended in the longitudinal direction to permit the hooks 462 to move longitudinally within the slots 464 a small distance.

The staple pusher bar 448 (FIGS. 50 and 51) defines a plurality of wedges 450. The stapler pusher bar 448 is directly above and in abutting relationship to the staple base 444.

Figure 52:
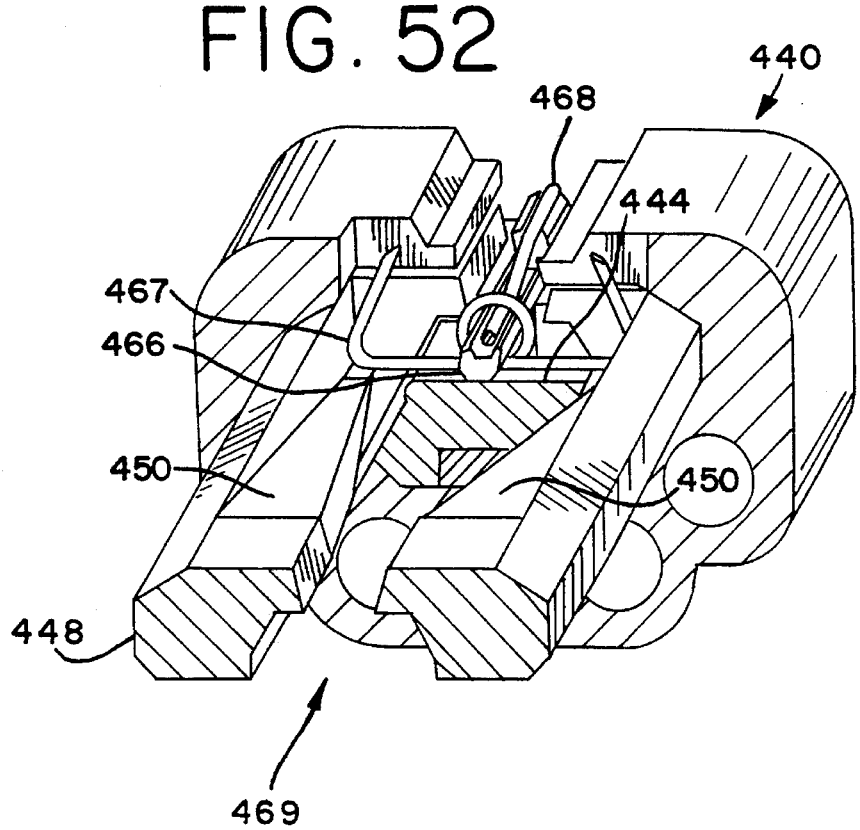
FIG. 52 is a perspective view of a portion of the cartridge shown in FIG. 50 wherein a portion of the cartridge housing has been removed to illustrate interior detail.
Figure 53:
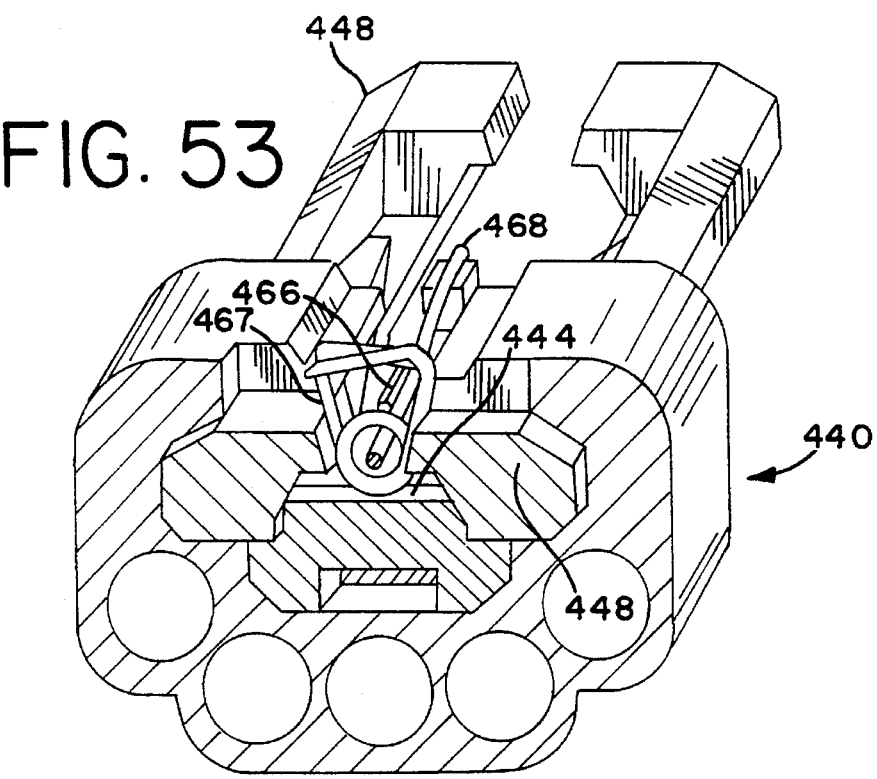
FIG. 53 is a perspective view of the cartridge as shown in FIG. 52 with the staple pusher bar and staple in a closed position.

The staple pusher bar 448 functions to close purse string staples in a fashion similar to the non-endoscopic instrument as described above. Referring to a preferred embodiment of the endoscopic version of the invention in FIGS. 52 and 53, each staple 467 is initially retained on a staple base 444 by a hook 466 which extends through the eyelet of the staple (FIG. 52). Suture 468 extends through the eyelet of the staple 467 and rests on the hook 466. The staple pusher bar 448 is moved longitudinally in the direction of the arrow 469. As the staple pusher bar 448 moves longitudinally, the wedges 450 lift and close the arms of the staple 467 (FIG. 53). The hook 466 retains the staple 467 on the staple base 444 until the hook 466 is disengaged after full closure of the staple 467 (FIG. 53).

Thus, the staple pusher bar 448 and staple base 444 form an assembly which functions as a staple closer mechanism. It will be appreciated that the staples, staple pusher bar and wedges may be constructed in a variety of designs similar to the variety of designs discussed above regarding the non-endoscopic aspect of the invention.

The assembly, interaction, and movement of the staples, suture, staple pusher bar, and retainer plate within the cartridge are illustrated in FIGS. 54–58. Referring to FIG. 54, the cartridge housing 442 contains the staple pusher bar 448, staple base 444 and retainer plate 446. The retainer plate 446 is initially positioned in a proximal position wherein the hooks 462 and 462*a* are positioned at the proximal end of the hook receiving slots 464 in the staple base 444 (hook 462*a* shown partially cut-away to reveal proximal end of slot 464).

Referring to FIG. 55, the staples 467 with suture 470 threaded therethrough are next placed in the notches 458 of the staple base 444. The staples 467 are oriented with their legs pointing upward. The suture 470 extends longitudinally, resting on top of the hooks 462.

Referring to FIG. 56, the hooks 462 are next moved longitudinally to the distal end of the hook-receiving slots 464 by longitudinally moving the retainer plate 446. As the hooks 464 are moved, they engage the eyelets of the staples 467. The cartridge 440 is now ready for use.

Figure 57:
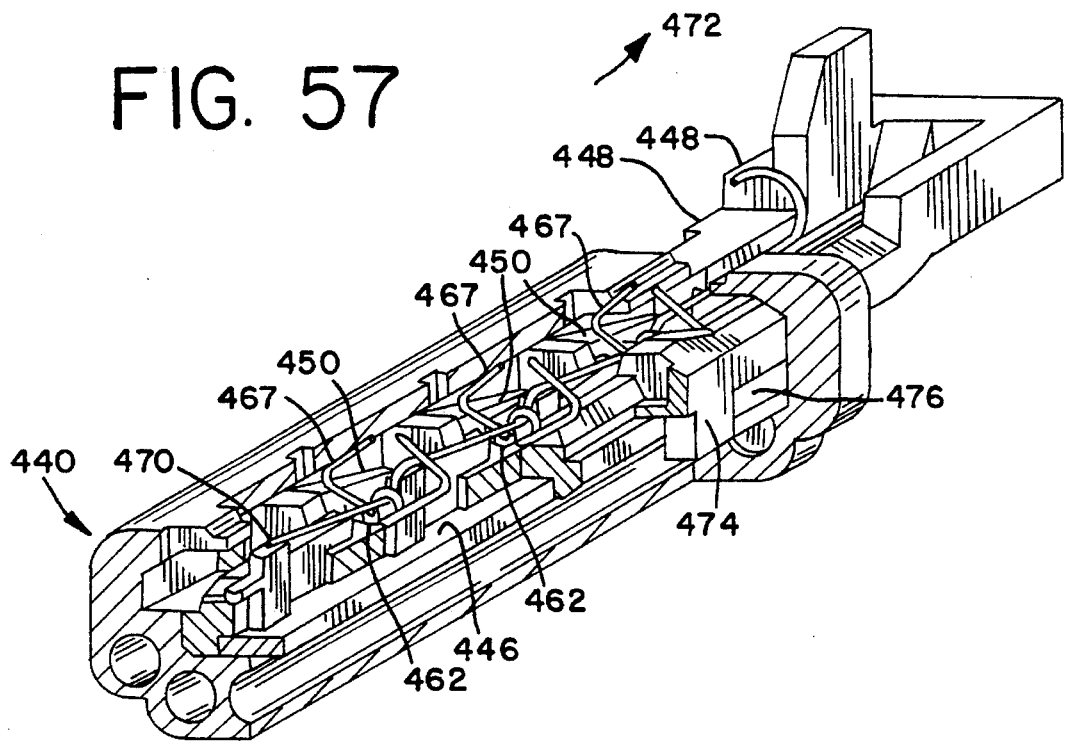
FIG. 57 is a perspective view of the cartridge, staples and suture as shown in FIG. 56 with the staple pusher bar and staples in a partially closed position.

Referring to FIG. 57, the sequence for closing the staples 467 is begun when the staple pusher bar 448 is moved proximally in the direction of the arrow 472. As the staple pusher bar 448 moves proximally, the wedges 450 on the staple pusher bar 448 contact the arms of the staples 467, and push the arms upwardly and inwardly toward a closed position. The eyelets of the staples are retained by the hooks 462 while the staple arms are moved toward the closed position.

Figure 58:
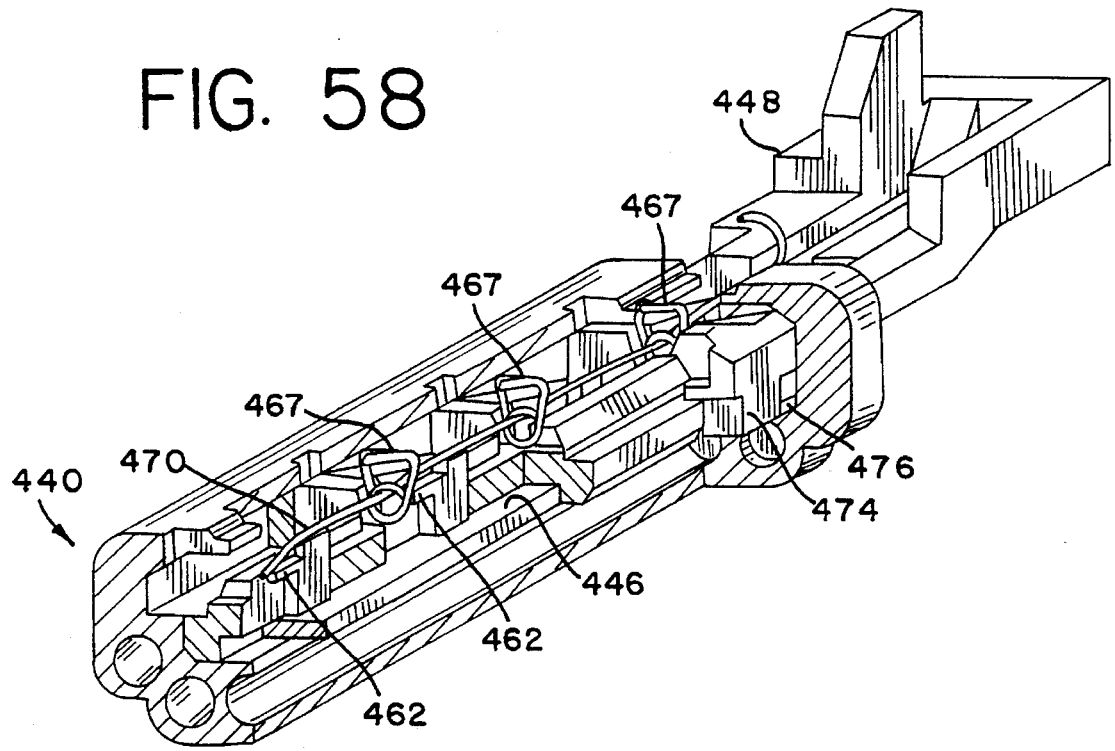
FIG. 58 is a perspective view of the cartridge, staples and suture shown in FIG. 57 with the staple pusher bar and staples in a fully closed position wherein the hooks are disengaged from the eyelets of the staples.

A protrusion 474 extends downwardly from the staple pusher bar 448 and contacts a wing 476 extending outwardly from the retainer plate 446 (FIG. 57). As the staple pusher bar 448 travels proximally, the protrusion 474 catches the wing 476 and pulls it proximally (FIGS. 57 and 58). Thus, the staple pusher bar 448 pulls the retainer plate 446 proximally as the staple pusher bar 448 completes its movement toward a proximal position. As the retainer plate 446 moves proximally, its hooks 462 are disengaged from the eyelets of the staples 467 (FIG. 58) and the staples 467 and suture 470 may be removed from the cartridge 440.

Figure 59:
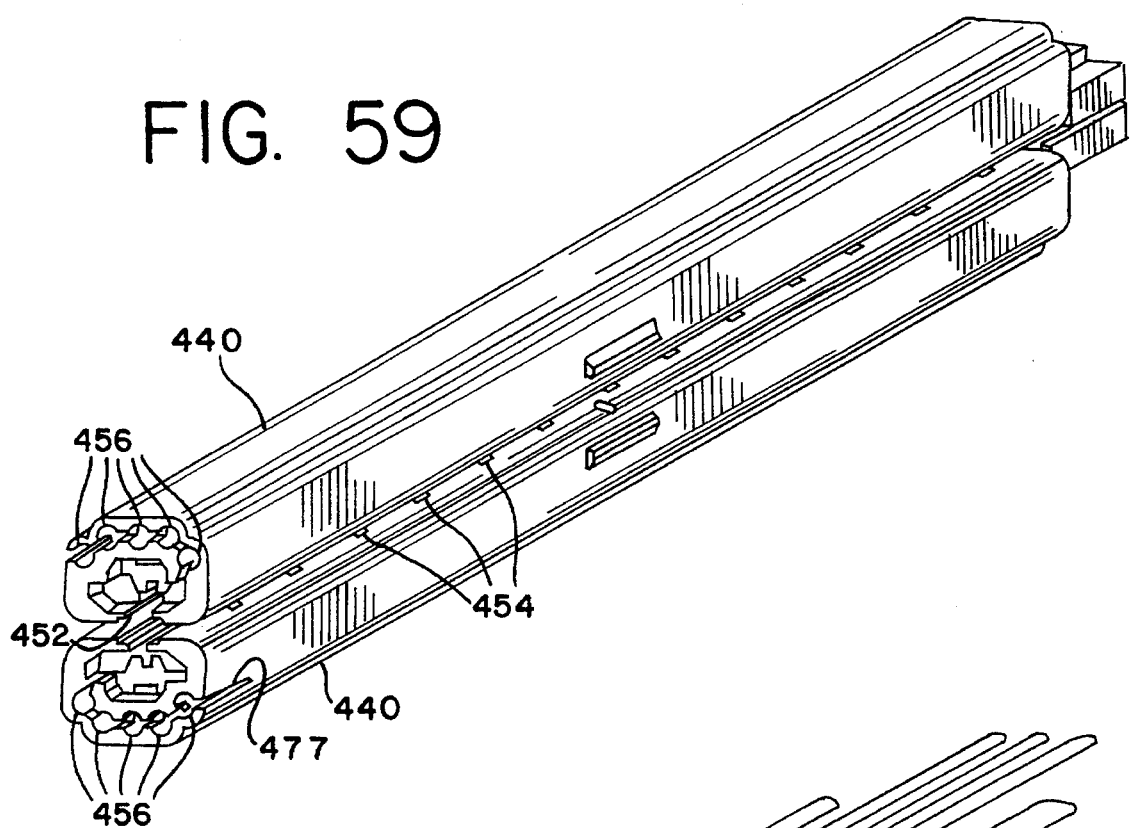
FIG. 59 is a perspective view of two cartridges for use in an endoscopic surgical instrument in accordance with the invention wherein the cartridges are positioned adjacent each other.
Figure 60:
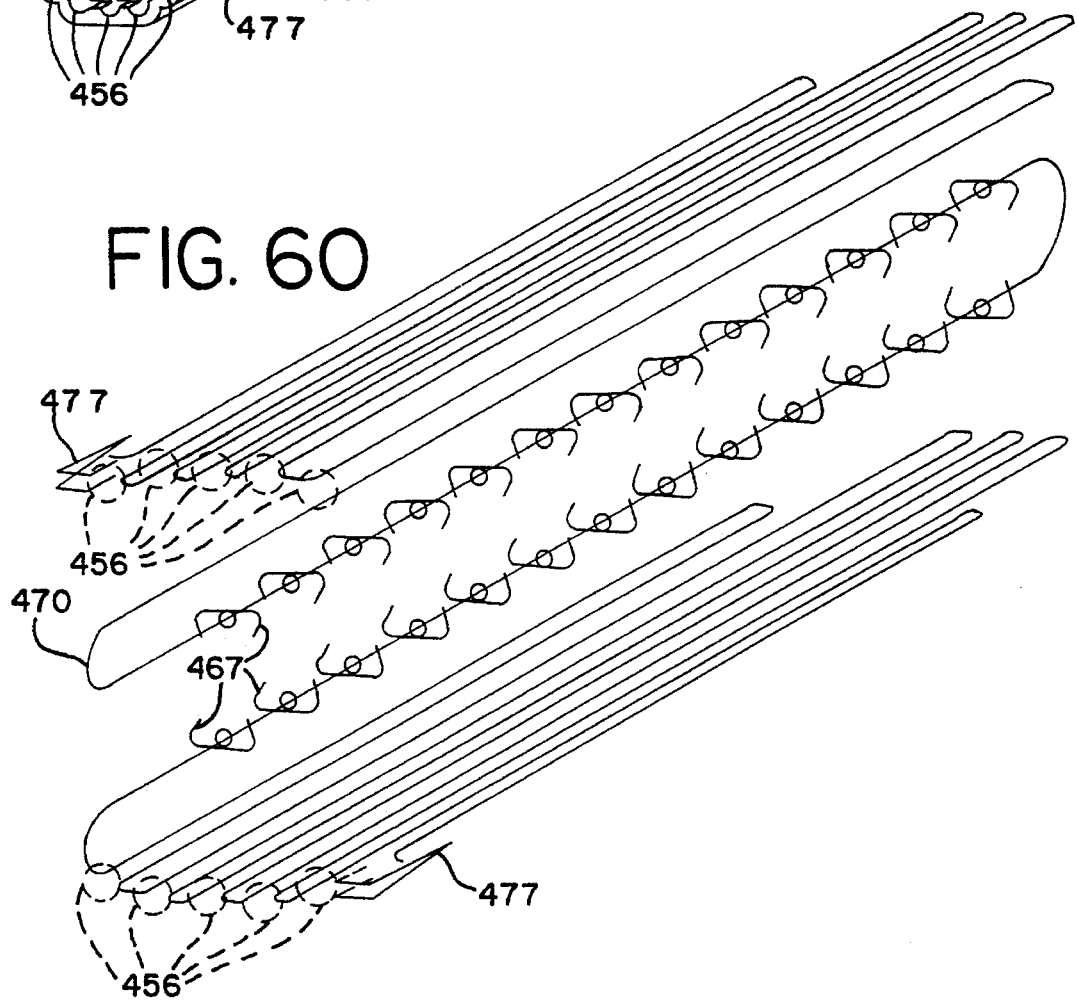
FIG. 60 is a schematic view of suture and staples as inserted into the two cartridges shown in FIG. 59.

Referring to FIG. 59, each cartridge 440 is matched with another cartridge 440, so that a single purse string may be threaded through the staples that are loaded in both cartridges 440. The two cartridges 440 are in juxtaposed relationship wherein the longitudinal slots 452 and the transverse staple receiving slots 454 in the cartridges 440 face each other. The suture is threaded through the eyelets in the staples of both cartridges. The extra length of the suture is inserted into the wells 456 of each cartridge 440. The ends of the suture are detachably inserted into a notch 477 on the side of each cartridge 440. FIG. 60 is a schematic illustration of the insertion of the suture 470 into the staples 467, notches 477, and each well 456, wherein each well 456 releasably contains a single loop of suture 470.

Figure 61:
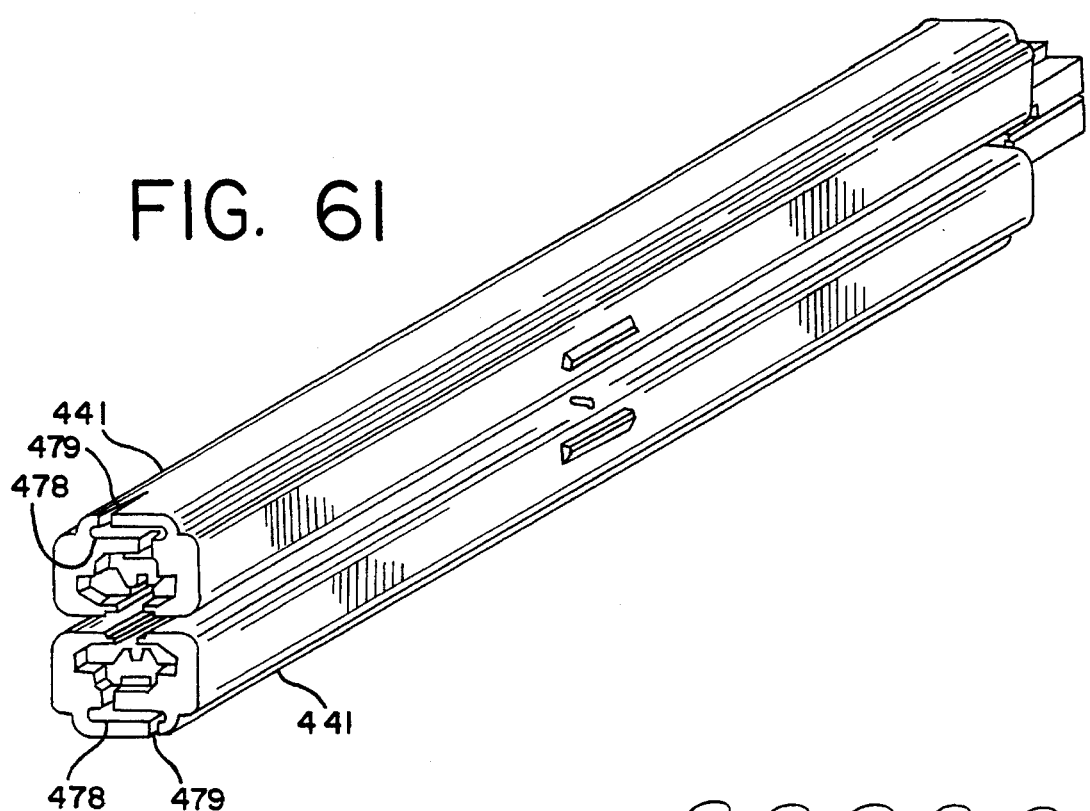
FIG. 61 is a perspective view of two cartridges for use in an endoscopic surgical instrument in accordance with the invention, each having a single suture well, wherein the cartridges are positioned adjacent each other.
Figure 62:
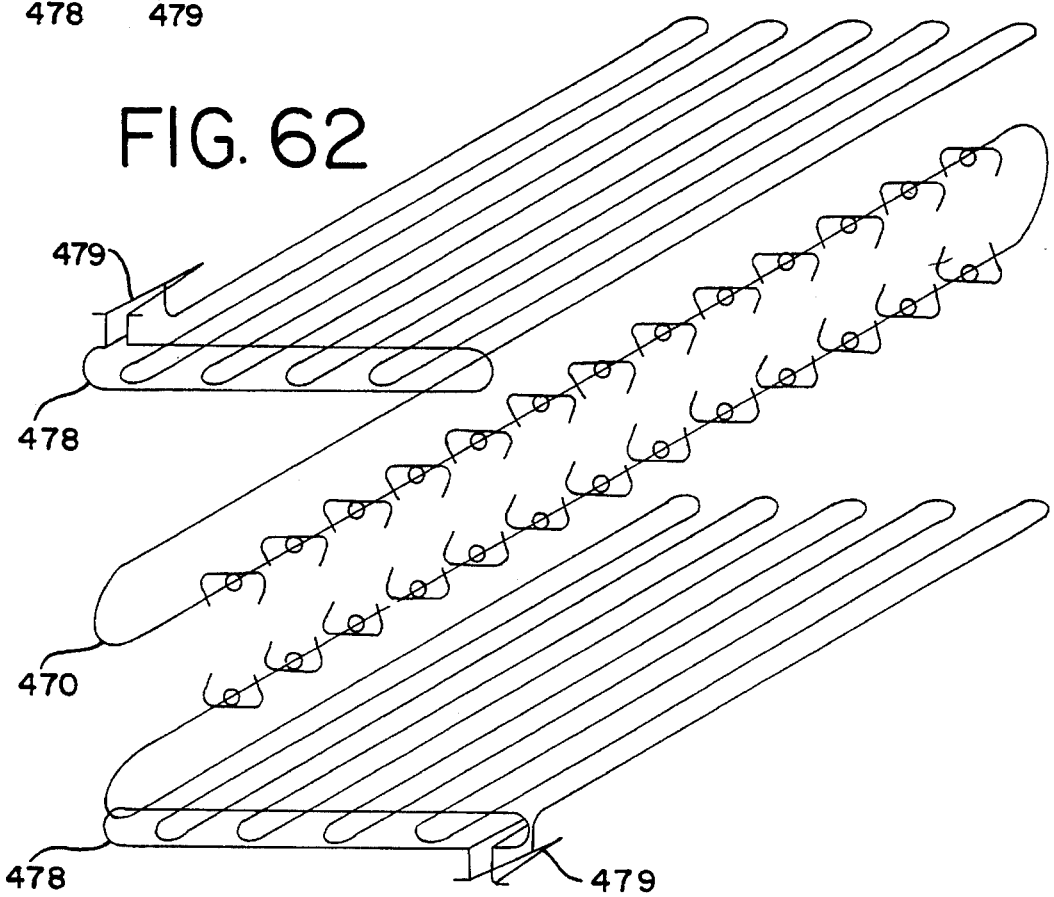
FIG. 62 is a schematic view of suture and staples as inserted into the two cartridges shown in FIG. 61.

The number of wells may be varied as needed. Alternatively, there may be a single well 478 in each cartridge 441 as shown in FIG. 61. The notches 479 for receiving the ends of the suture may be on the top and bottom sides of the cartridges 440. Multiple loops of suture 470 are releasably contained in each well 478 as schematically shown in FIG. 62.

Referring to FIGS. 63 and 64, a cartridge holder 480 is used to temporarily hold two cartridges 440 in juxtaposed relationship before they are inserted into the jaws of the stapler. The cartridge holder 480 has small posts 482 extending upwardly and downwardly. The posts 482 fit into corresponding holes 484 in the cartridges 440 with a detachable press fit. The two cartridges 440 as held by the cartridge holder 480 (FIG. 64) may be conveniently stored and eventually placed into the open jaws of a stapler according to the invention.

Figure 65:
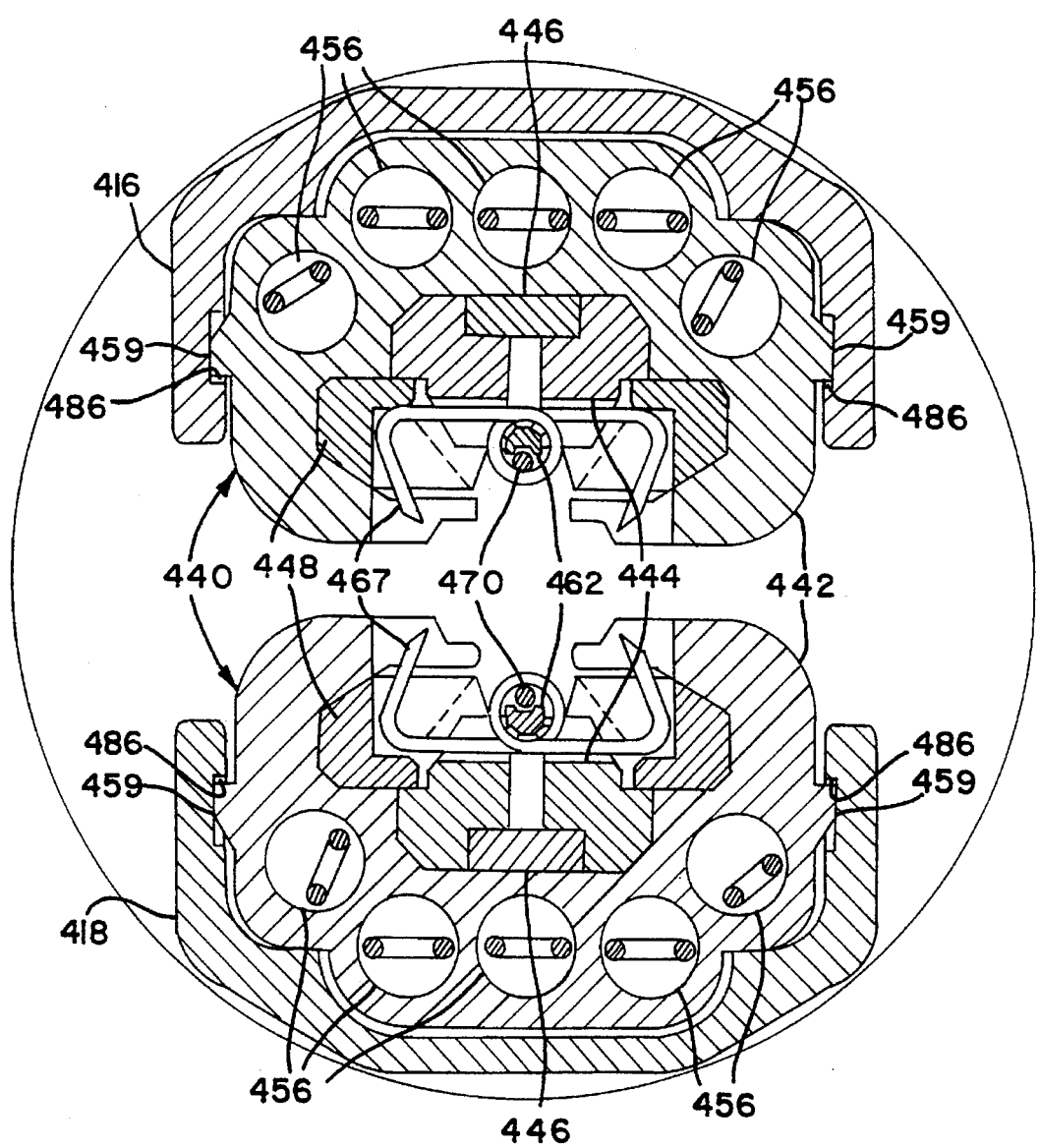
FIG. 65 is an enlarged cross-sectional view of two fully-loaded cartridges for use in an endoscopic surgical instrument in accordance with the invention wherein the cartridges are positioned adjacent each other.

FIG. 65 illustrates a cross-sectional view of two fully loaded cartridges 440, including cartridge housings 442, staple pusher bars 448, retainer plates 446, hooks 462, staple bases 444, staples 467, catches 459, wells 456, and suture 470, as loaded into a pair of jaws 416 and 418 having retaining lips 486.

Referring to FIGS. 66 and 67, the jaws 416 and 418 are movable between an open position (FIG. 66) and a closed position (FIG. 67). Preferably, the upper jaw 416 is movable while the lower jaw 418 remains stationary. A spring 486 biases the upper jaw 416 toward the open position.

A wedge mechanism actuates the movable upper jaw 416 (FIGS. 66 and 67). The wedge 488 is attached to a longitudinally-extending drive rod 490 which extends proximally within the outer tube 420 and into the handle 424. The wedge 488 and drive rod 490 are slidably contained within the outer tube 420 and handle 424. A lever 426 in the handle 424 moves the wedge 488 and drive rod 490 longitudinally.

When the lever 426 and jaw 416 are opened (FIG. 66), the wedge 488 is retracted from the movable upper jaw 416. When the lever 426 is closed (FIG. 67), the wedge 488 is driven under the rear end 491 of the movable jaw 416, thus closing the Jaw.

The connection 492 between the wedge 488 and drive rod 490 permits rotation of the wedge 488 relative to the drive rod 490 when the endoscopic portion 412 is rotated relative to the handle portion 414. Preferably, the connection 492 is of the ball and socket type.

Referring back to FIGS. 47–49, an articulation linkage assembly 493 articulates the jaw portion 415. The linkage assembly 493 includes an articulation link 494 that is connected to the fixed jaw. The connection is offset from the axis 496 of articulation of the jaw. A drive link 498 extends proximally from the articulation link 494 and is connected to a longitudinally-extending articulation tube 500. The articulation tube 500 slides longitudinally inside the outer tube 420.

The articulation linkage 493 is controlled by an articulation crank 434 in the handle 424 (FIGS. 47 and 49). A driver tube 502 extends distally from the crank 434 and is rotatably fitted with the articulation tube 500 extending proximally from the linkage 493. Preferably, the connection between the driver tube 502 and articulation tube 500 includes a radial flange 504 extending from the articulation tube 500 and fitting to a circumferential groove inside the driver tube 502.

The driver tube 502 has a vertical slide portion 506 at its proximal end (FIGS. 47 and 49). A bar 508 affixed to the crank 434 extends laterally from the crank into the slide. The bar 508 slides vertically in the slide portion 506 so as to permit the crank 434 to rotate and thereby move the drive tube 504 distally and proximally.

The interaction of the articulation linkage 493 and crank 434 is seen in FIGS. 47–49. In FIG. 47, the jaw portion 415 is fully extended. As the crank 434 is turned counterclockwise, the articulation linkage 493 is pulled in a proximal direction, and the jaw portion 415 variably articulates on axis 496 (45° in FIG. 48, 90° in FIG. 49). Conversely, when the crank 434 is rotated clockwise, the entire articulation linkage 493 is driven in a distal direction and the jaw portion 415 returns toward its fully extended position (FIG. 47).

Figure 68:
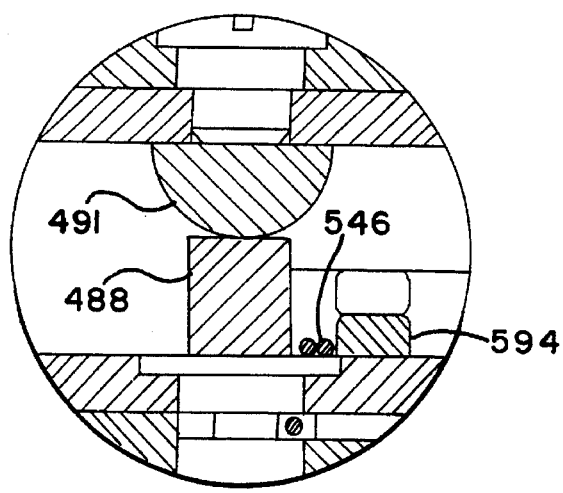
FIG. 68 is an enlarged cross-sectional view taken along the line 68—68 in FIG. 67.

The jaws are movable between their opened and closed positions in any angle of articulation. The ability to open and close while articulated is facilitated by the design of the rear end 491 of the movable upper jaw 416. Referring to FIGS. 66 and 68, the rear end 491 of the movable upper jaw has a hemispherical lower surface. The hemispherical lower surface permits the wedge 488 to fit under and lift up the rear end 491 of the movable jaw 416 and thereby close the movable jaw 416 when the jaws are articulated to any angle.

Figure 69:
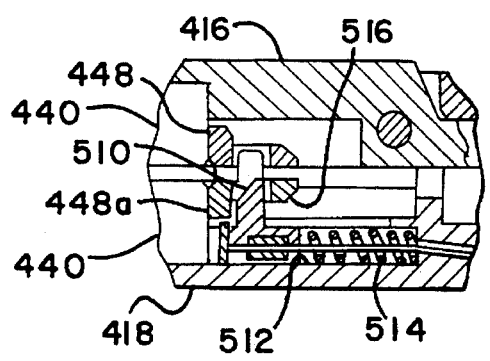
FIG. 69 is an elevational view, partially broken away, of the firing mechanism of an endoscopic surgical instrument in accordance with the invention.
Figure 70:
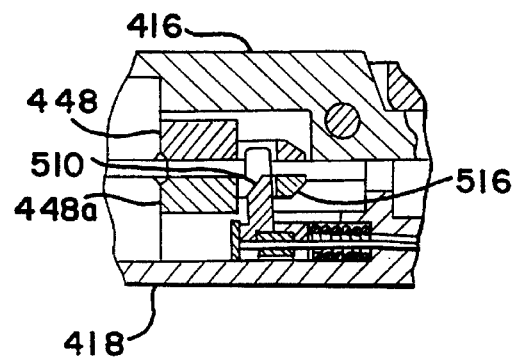
FIG. 70 is an elevational view of the firing mechanism as shown in FIG. 69 with the firing pin having been fired.

The firing mechanism for moving the staple pusher bars is illustrated in FIGS. 69 and 70. Referring to FIG. 69, a firing pin 510 is longitudinally slidable within a slotted cylinder 512 in the lower jaw 418. A spring 514 in the cylinder 512 biases the pin 510 toward a distal position as shown. The pin 510 extends upwardly and engages the proximal end portion 516 of the lower staple pusher bar 448a that extends proximally from the cartridges 440.

Referring to FIG. 70, the staples in the cartridges are fired when the firing pin 510 moves in a proximal direction. As the pin 510 moves, it engages and pulls the lower staple pusher bar 448a in a proximal direction. Thus, the staples in the lower jaw 418 are fired. The staples in the upper jaw 416 are fired at the same time due to the interlocking arrangement of the staple pusher bars 448 and 448a in the upper and lower jaws. Thus, the upper staple pusher bar 448 moves proximally with the lower staple pusher bar 448a.

The staple pusher bar in accordance with the invention is configured so as to interlock with another staple pusher bar of the same design that is placed adjacent to and in a mirror-image relationship to it. Thus, when two cartridges are loaded in an adjacent and mirror-image relationship to each other in the jaws of the endoscopic suture stapler as described herein, the staple pusher bars of each cartridge are interlocked, and each bar will coact with and draw the other when moved in a proximal direction.

Referring to FIGS. 63A and 63B, each staple pusher bar 448 and 448a has a fin 518 and a cross member 520. Referring to FIG. 64A, the interconnection of the staple pusher bars occurs when the fin 518 of one stapler pusher bar 448 catches and holds the cross member 520 of the other staple pusher bar 448a as it moves in a proximal direction.

The coaction of the staple pusher bars results in a staple cartridge which is uniquely configured to coact with another cartridge of a substantially similar design. Thus, a single cartridge design can be used to fulfill the requirements of placing coacting cartridges in the upper and lower jaws of a suture stapler.

Figure 71:
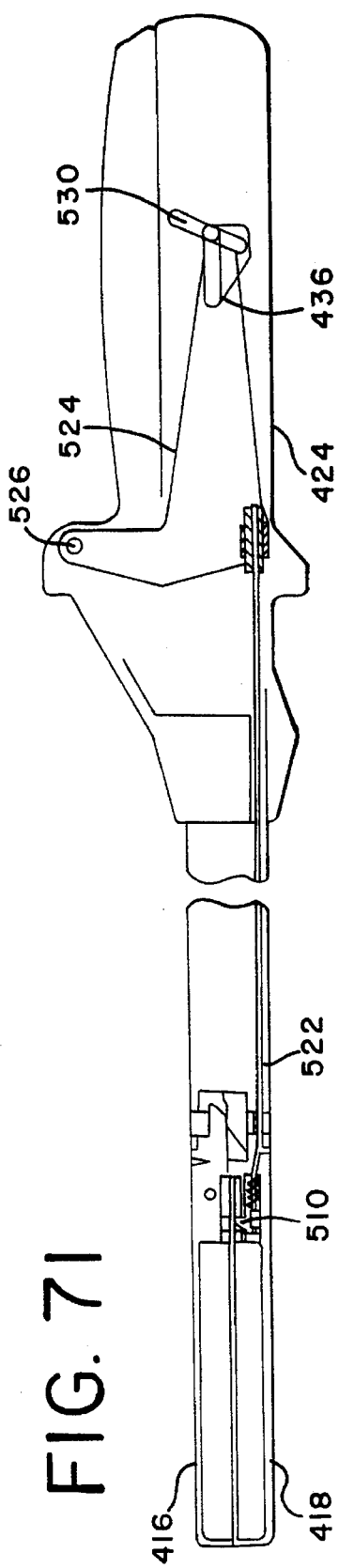
FIG. 71 is an elevational view, partially in cross-section, of the instrument shown in FIG. 45 illustrating the firing mechanism and the trigger mechanism.
Figure 72:
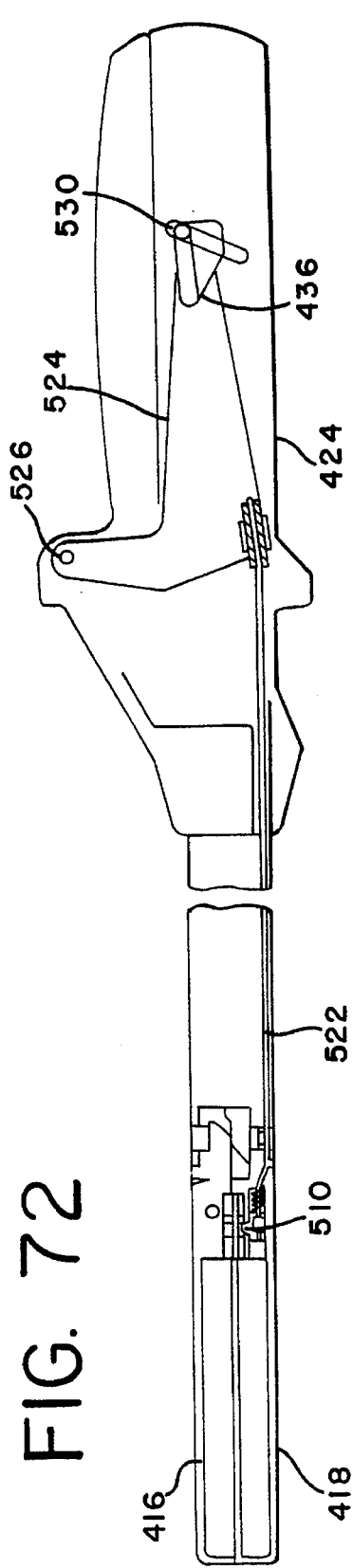
FIG. 72 is an elevational view of the instrument as shown in FIG. 71 with the firing pin and trigger being shown in the fired position.

The firing mechanism is actuated by a trigger mechanism as shown in FIGS. 71 and 72. In FIG. 71, the firing mechanism is ready to be fired. A firing cable 522 is connected to the firing pin 510 and extends proximally into the handle 424. The cable 522 is attached to a plate 524 inside the handle 424. The plate 524 is attached to the handle with a hinge pin 526. The plate 524 rotates slightly about the hinge pin 526 within the confines of the interior of the handle 424. A trigger 436 extends laterally from the plate and through a slot 530 in the handle 424 (also shown in FIG. 45).

The firing mechanism is fired by moving the trigger 436 upwardly from a pre-firing position (FIG. 71) to a fired position (FIG. 72). As the trigger 436 moves upwardly, the plate 524 rotates counterclockwise about its hinge 526 and the cable 522 is pulled by the plate 524 in a proximal direction. As the cable 522 moves, it draws the firing pin 510 in a proximal direction. Thus, the firing mechanism is actuated.

Figure 73:
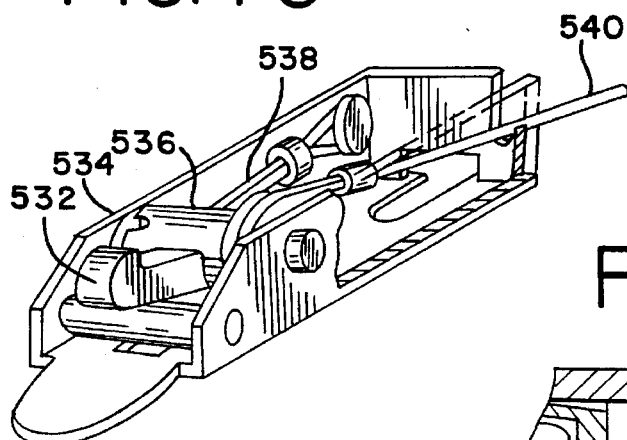
FIG. 73 is a perspective view, partially broken away, of an alternative embodiment of the firing mechanism in accordance with the invention.
Figure 74:
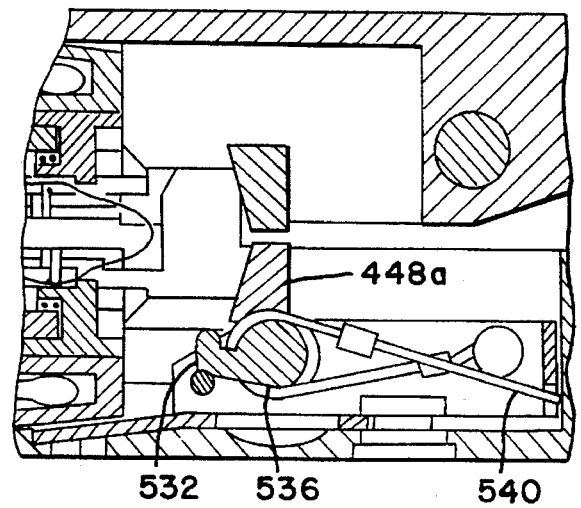
FIG. 74 is an enlarged cross-sectional view of a portion of the firing mechanism shown in FIG. 73.

An alternative firing pin mechanism is shown in FIGS. 73 and 74. Referring to FIG. 73, the alternative firing pin-mechanism includes a firing pin 532 that is rotatably mounted in a box frame 534. The firing pin 532 extends from a rotating cylinder 536 that extends between the sides of the frame 534. An elastically stretchable band 538 is attached on a wall of the frame 534 and extends around a portion of the cylinder 536 before attaching to the cylinder 536. The stretchable band 538 biases the rotation of the cylinder 536 in a counterclockwise direction. The firing cable 540 is attached to the cylinder and wraps around it at least one full revolution before extending proximally toward the trigger mechanism.

Referring to FIG. 74, the alternative firing pin mechanism is fired when the firing cable 540 moves proximally and causes the cylinder 536 and firing pin 532 to rotate clockwise. As the cylinder and pin rotate, the firing pin engages the lower staple pusher bar 448a and moves it in a proximal direction.

Figure 75:
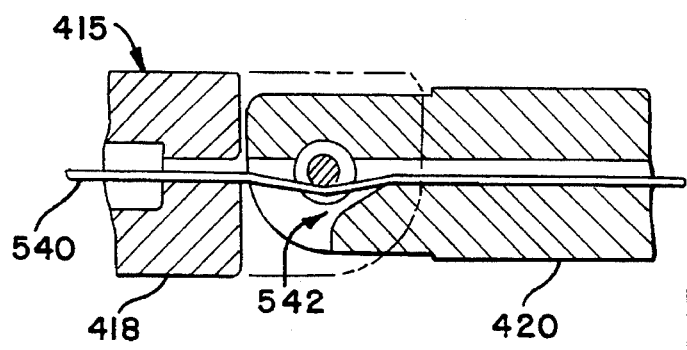
FIG. 75 is a cross-sectional view of a portion of the hinge structure connecting the jaw portion and the outer tube.
Figure 76:
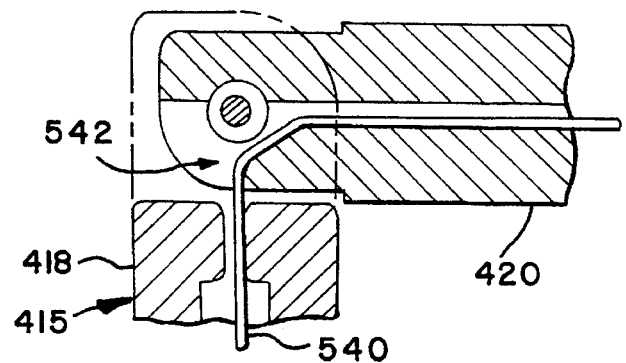
FIG. 76 is a cross-sectional view of the hinge structure as shown in FIG. 75 with the jaw portion articulated 90°.

Referring to FIGS. 75 and 76, the firing cable 540 is flexible in order to permit it to bend where it passes from the lower jaw 418 and into the outer tube 420 when the jaw portion 415 is articulated to an angled position. In FIG. 75, the jaw portion 415 is in a parallel orientation. In FIG. 76, the jaw portion 415 is in a 90° angled orientation. The outer surface of the corner structure 542 in the outer tube 420 (FIG. 76) is rounded and smooth in order to permit the cable 540 to slide longitudinally around it easily.

Figure 77:
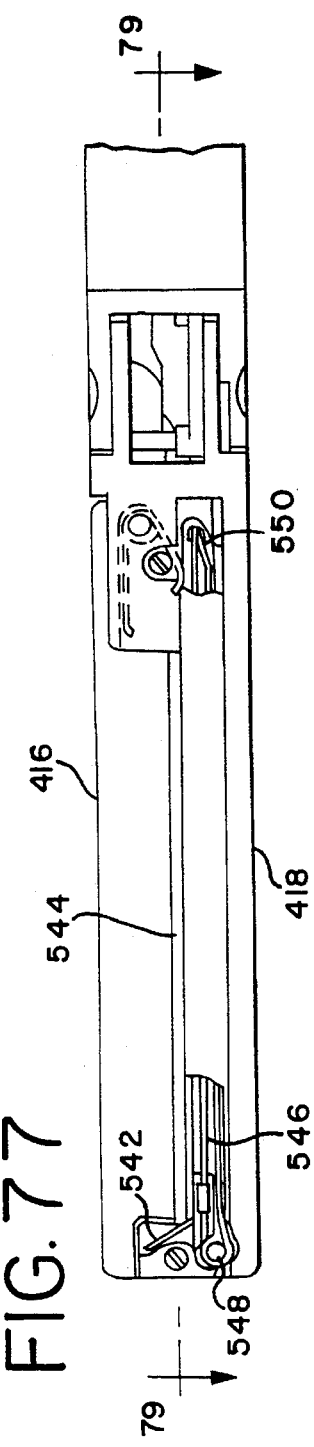
FIG. 77 is an elevational view of the jaw portion of the instrument shown in FIG. 45 with portions broken away to illustrate interior detail.
Figure 78:
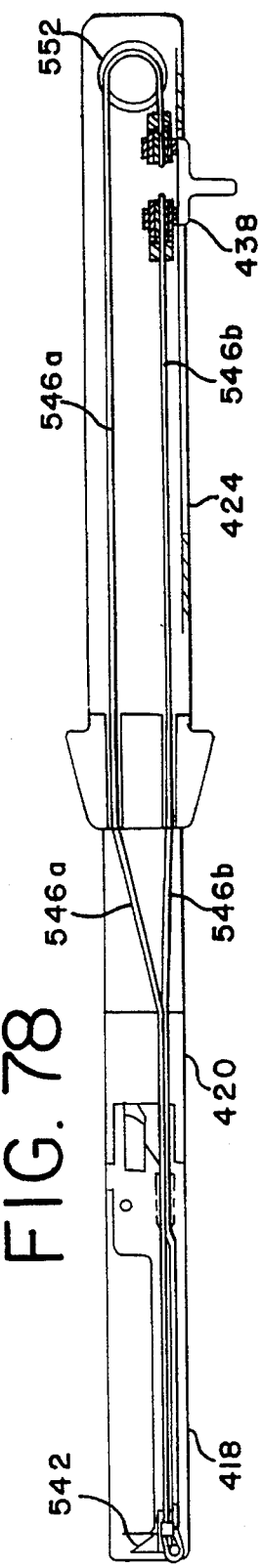
FIG. 78 is an elevational view of the instrument shown in FIG. 45 with portions broken away to illustrate the cutting blade and cutting blade actuating mechanism.
Figure 79:
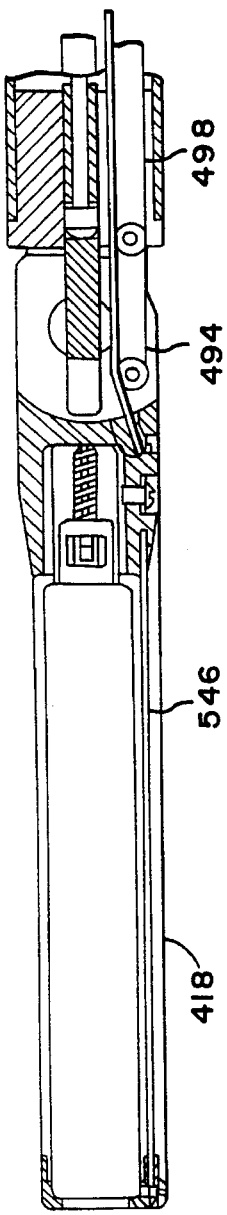
FIG. 79 is a cross-sectional view of the jaw portion taken along the line 79—79 in FIG. 77.

The blade and blade actuating mechanism are shown in FIGS. 77–79. Referring to FIG. 77, the blade 542 is slidably mounted on a track 544 on the lower jaw 418. The blade 542 extends upwardly and moves adjacent to the lateral surface of both jaws. The blade 542 is slidable along the track between a distal position and a proximal position.

A blade cable 546 that is affixed to the blade 542 and extends both proximally and distally from the blade 542 for pulling the blade in either a proximal or distal direction. The cable 546 is looped around a laterally-extending rod 548 at the distal end of the track and two strands extend proximally from the rod 548 along the track 544. At the proximal end of the track, the two strands of the cable 546 enter the interior of the lower jaw 418 through an aperture 550.

Referring to FIG. 78, the two cable strands 546a and 546b divide in the outer tube 420 and remain divided as they extend proximally into the handle 424. Strand 546a is strung around a pulley 552 at the proximal end of the handle 424. The two strands 546a and 546b meet at a blade actuator 438.

The blade actuator 438 is attached to the blade cable 546 within the handle 424. The blade actuator 438 extends laterally outside the handle 424 through a longitudinally-extending slot 556 (see FIG. 45) in the handle 424. The blade actuator 438 is manipulated by a user of the instrument in order to move the blade 542 along the track 544 in the lower jaw 418. The blade actuator 438 is moved distally in order to move the blade 542 proximally and, vice versa, the actuator 438 is moved proximally in order to move the blade 542 distally.

FIG. 79 illustrates the positioning of the cable 546 in the lateral portion of the lower jaw 418 and adjacent the articulation link 494 and drive link 498 (also seen in FIGS. 48, 49 and 68). Because of the flexibility of the blade cable 546, it bends with the jaw portion 415 when the Jaw portion is articulated and moved to an angled position (FIGS. 48 and 49). The links 494 and 498 have rounded smooth surfaces that permit the cable 546 to slide around them easily.

Figure 80:
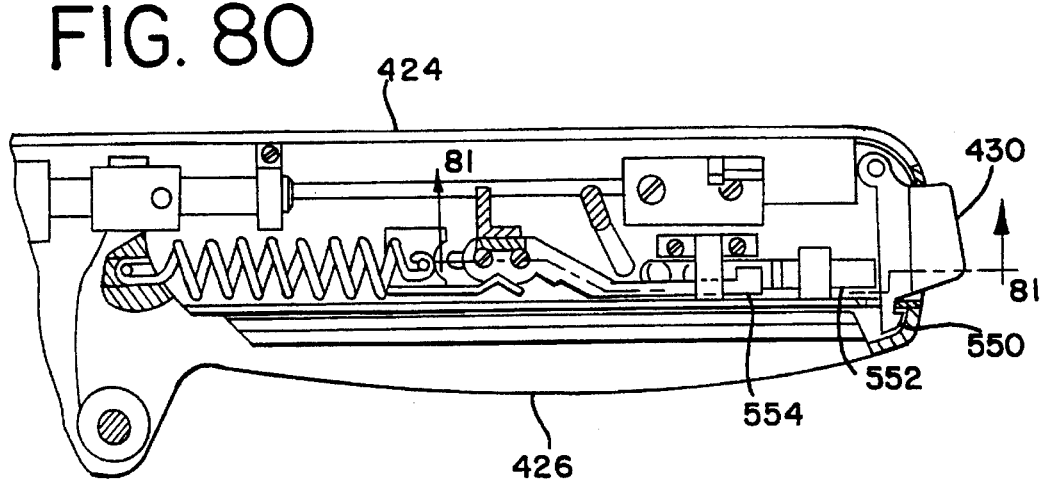
FIG. 80 is an elevational view, partially broken away, of the handle of an endoscopic surgical instrument in accordance with the invention wherein the handle lever faces downwardly.

Referring to FIG. 80, a latch 430 for latching the lever 426 to the handle 424 in the closed position is shown. The latch 430 is hingeably attached at the proximal end of the handle 424. The latch has a catch 550 which engages the lever 426 and holds it in the closed position. In order to release the lever 426, the latch 430 is depressed so as to disengage it from the lever 426 and permit the lever 426 to move from its closed position to an open position (shown as lever 426 in phantom lines in FIG. 83).

Figure 81:
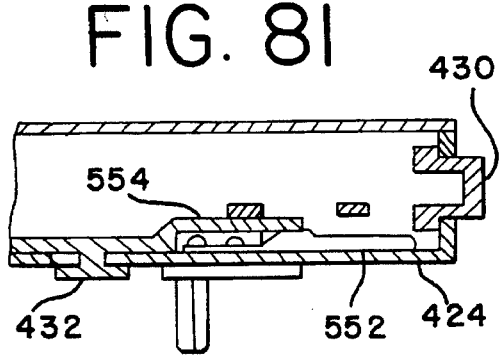
FIG. 81 is a cross-sectional view of the handle taken along the line 81—81 in FIG. 80.
Figure 82:
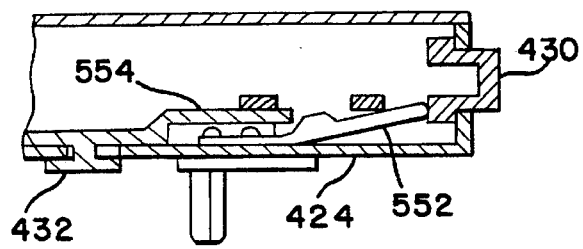
FIG. 82 is a cross-sectional view of the handle as shown in FIG. 81 with the slidable retainer located in a distal position.

A locking mechanism for locking the latch 430 and lever 426 in the closed position is adjacent the latch in the interior of the handle 424 (FIGS. 80–82). Referring to FIG. 81, an elastically bendable stop 552 is connected to the interior face of one side of the handle 424. The stop 552 is biased to angle away from the inner face of the side of the handle 424. However a retainer 554, also mounted to the inner face of the side of the handle 424, engages the stop 552 and maintains it in a position flush against the inner face of the handle. In this flush position, the stop 552 does not abut the inside face of the latch 430 and permits the latch to be depressed. Thus, when the stop 552 is disengaged from the latch 430, the latch is unlocked.

Referring to FIG. 82, the retainer 554 is slidable toward a distal position wherein it disengages the stop 552' and permits the stop 552 to move to its unstressed position angling away from the interior face of the side of the handle 424. In this position, the stop 552 abuts the inside face of the latch 430 and prevents the latch 430 from being depressed. Thus, when the stop 552 engages the latch 430, the latch is locked.

A portion of the retainer 554 extends laterally through a longitudinal slot in the side of the handle where it is connected to a lock button 432 (FIGS. 45, 81–83). The lock button 432 is manipulated by the user of the instrument in order to move the slidable retainer 554 for locking and unlocking the latch 430.

Figure 83:
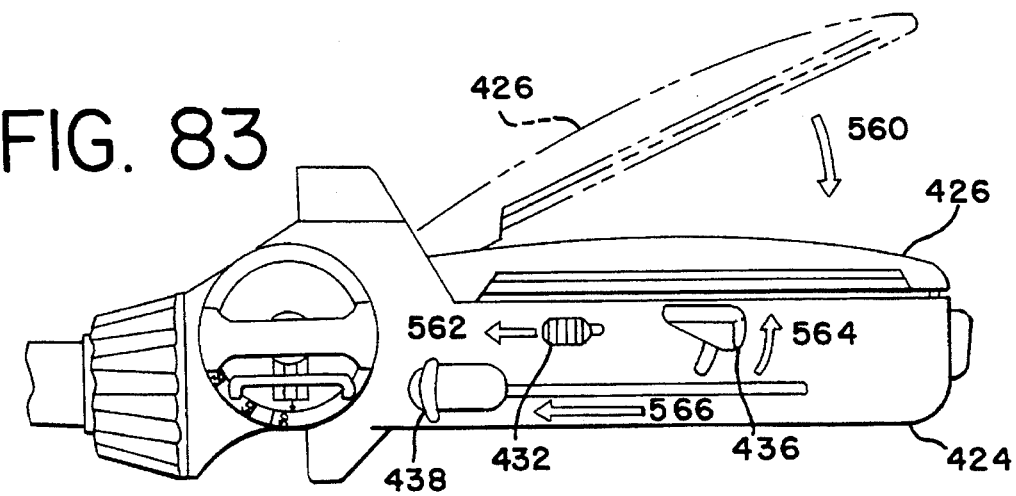
FIG. 83 is an elevational view of the handle of an endoscopic surgical instrument in accordance with the invention with the lever shown in an open position in phantom lines.

The sequence of operation of the several actuators and buttons is illustrated in FIG. 83. First, the lever 426 is closed by moving it in the direction of the arrow 560 in order to close the jaws. Second, the lock button 432 is moved in the direction of the arrow 562 in order to lock the lever 426 in the closed position. Third, the trigger 436 is moved in the direction of the arrow 564 in order to fire the staples. Fourth, the blade actuator 438 is moved in the direction of the arrow 566 in order to move the cutting blade.

Figure 84:
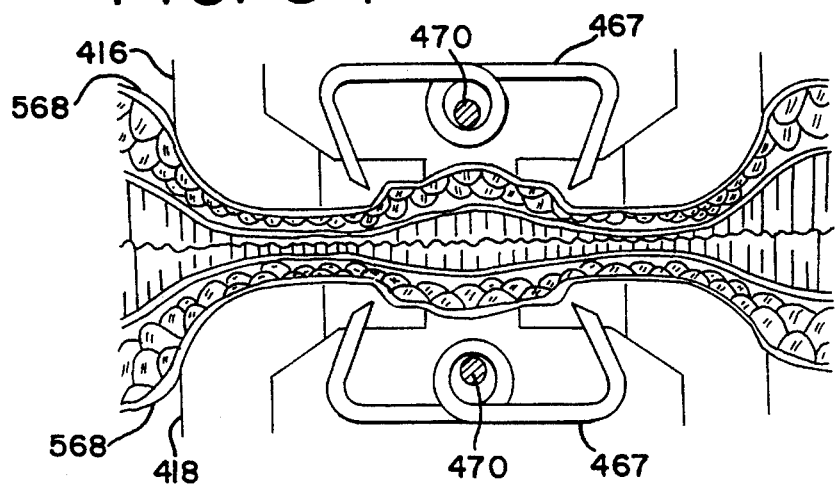
FIG. 84 is a schematic representation of tissue compressed between two cartridges for use in an endoscopic surgical instrument in accordance with the invention.
Figure 85:
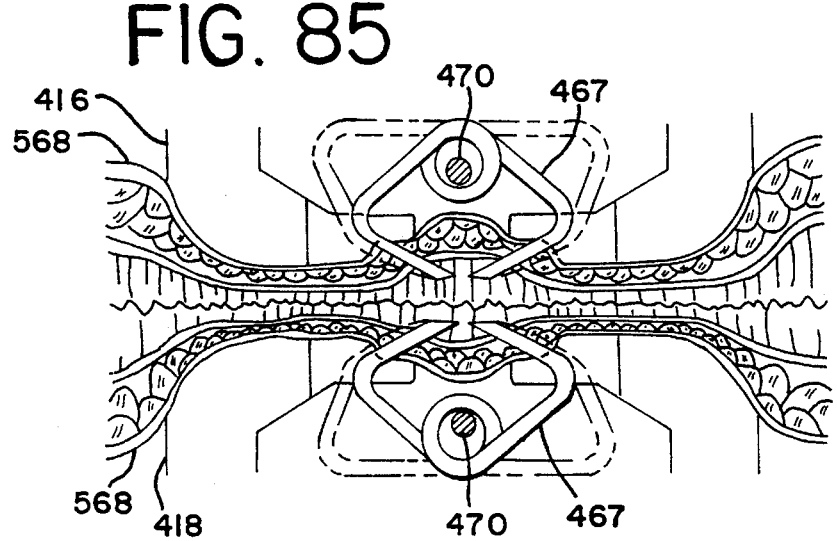
FIG. 85 is a view of the tissue and cartridges shown in FIG. 84 with the staples deformed to a partially closed position.
Figure 86:
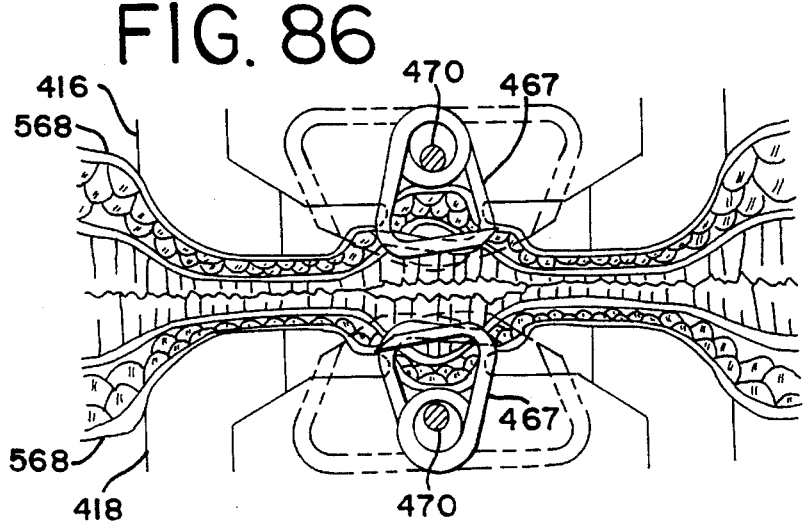
FIG. 86 is a view of the tissue and cartridges shown in FIG. 85 with the staples in a fully closed position.

The insertion of the staples 467 from the jaws 416 and 418 into tissue 568 is illustrated in FIGS. 84–86. In FIG. 84, the jaws 416 and 418 are closed. They compress tissue 568 between them. The staples 467 are ready for firing. In FIG. 85, the staples 467 are partially bent and have pierced the tissue 568. In FIG. 86, the staples 467 are fully bent wherein their tips grip and hold the tissue 568. The suture 470 is retained in the eyelets of the staples 467. Each staple 467 pierces and retains a single layer of tissue 568. Therefore, when the jaws 416 and 418 are removed, the two layers of tissue are free to separate as shown in FIG. 14.

Figure 87:
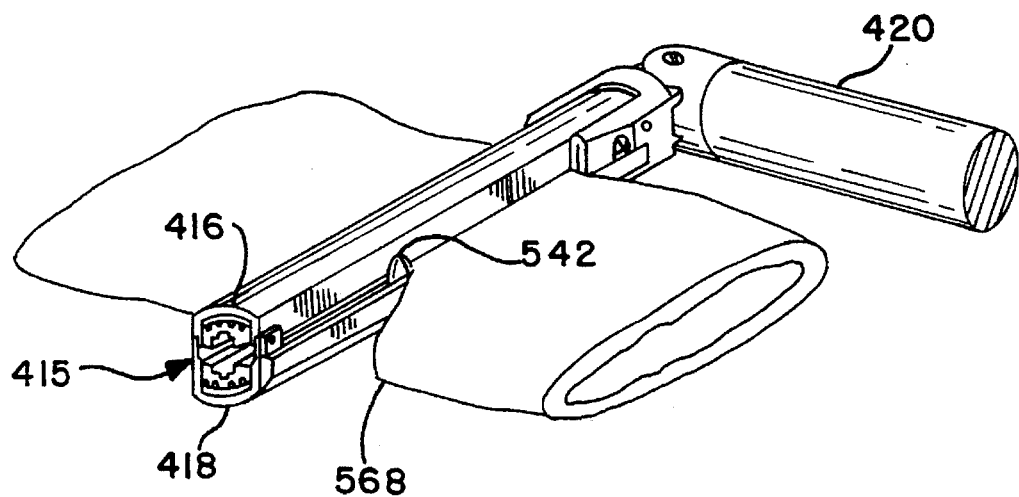
FIG. 87 is a partial perspective view of body tissue compressed between two jaws of an endoscopic surgical instrument in accordance with the invention wherein the body tissue is partially transected.
Figure 88:
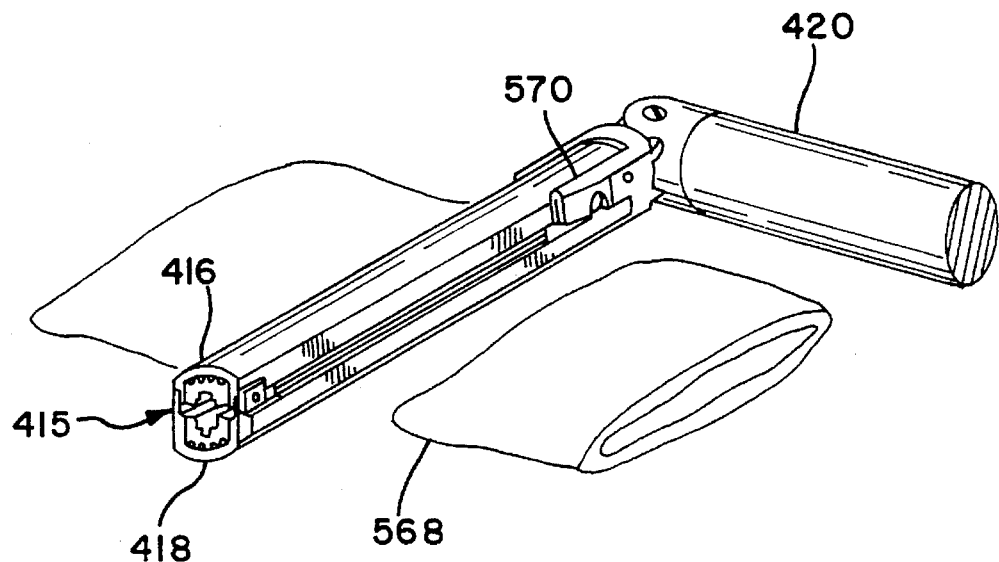
FIG. 88 is a partial perspective view of the body tissue and jaw portions shown in FIG. 87 wherein the body tissue is fully transected.

The cutting operation is illustrated in Figs. 87 and 88. In FIG. 87, the jaws 416 and 418 are closed. The jaw portion 415 is shown articulated 90°. The blade 542 is shown as it moves proximally and cuts tissue 568 away from the jaws 416 and 418. In FIG. 88, the blade has completed its travel proximally and resides within a blade housing 570. The tissue 568 is fully cut and separated.

The apparatus described herein is usable in a method for applying purse string suture and staples to a body tissue endoscopically. In the preferred method, a fully loaded stapler 410, with staple cartridges 440 inserted in the jaws 416 and 418 and the jaws closed as shown in FIG. 45, is inserted into and through a trocar cannula. The jaw portion 415 extends from the trocar cannula and into a body cavity. The jaw portion 415 is articulated as necessary to be positioned adjacent body tissue 568. The jaws are then opened by moving the lever 426 to an open position. Body tissue 568 is inserted between the jaws 416 and 418. Preferably, the body tissue has two layers that are pressed together, such as two layers of a tubular organ as shown in FIG. 14. The jaws 416 and 418 are then closed by moving the lever 426 to the closed position. The lever is latched closed and the lock 432 is actuated to lock the lever.

The staples are then fired by distal movement of the firing trigger 436. The knife blade 542 is then actuated by the knife blade actuator 438. The knife blade is moved proximally in order to cut the tissue.

After the body tissue is cut, the lock button 432 is moved proximally to unlock the latch 430. The latch 430 is depressed and the lever 426 is opened to open the jaws 416 and 418. As the jaws 416 and 418 are opened, each end of the purse string suture 470 is retained in notches 477 in the upper and lower jaws (See FIGS. 59 and 60). The jaws are moved away from the body tissue containing the purse string staples 467 and suture 470. As the jaws are moved away from the tissue, the suture slips from the wells 456 and eventually the notches 477 in the jaws.

The result is the application of a series of purse string staples having eyelets extending from the surface of the body tissue and a purse string suture extending through each of the eyelets similar to the staples 50 and suture 80 as shown in FIG. 14. Preferably, each staple penetrates into only one layer of body tissue. The purse string suture may then be tightened and knotted using conventional techniques as necessary according to the needs of the particular surgery being performed.

The invention in its broader aspects is not limited to the specific details of the preferred embodiments shown and described, and those skilled in the art will recognize that the invention can be practiced with modification within the spirit and scope of the appended claims.

What is claimed:

1. A cartridge for holding surgical staples and suture comprising:

a cartridge housing defining a) an interior portion, b) a central longitudinal slot for permitting passage of a longitudinally extending suture out of said cartridge housing, and c) a plurality of staple receiving slots for permitting passage of staples out of said cartridge;

a staple base within said housing for releasably holding staples;

a retainer plate within said housing, said retainer plate having a plurality of hooks for releasably engaging said staples; and a staple pusher bar within said housing for closing said staples, said staple pusher bar being longitudinally movable from an open position wherein said staples are open to a closed position wherein said staples are closed.

2. A cartridge in accordance with claim 1 wherein said retainer plate is movable from an engaged position to a disengaged position.

3. A cartridge in accordance with claim 1 wherein said cartridge housing defines a wall for releasably containing a suture string.

4. A cartridge in accordance with claim 1 wherein said cartridge housing defines a plurality of wells for releasably containing a suture.

5. A cartridge in accordance with claim 4 wherein the number of said wells is in the range of about two to about ten.

6. A staple cartridge, comprising:

a plurality of staples and an elongated housing including a tissue engaging surface, a plurality of transverse slots extending into said housing from said tissue engaging surface for receiving an individual staple therein, and an elongated central slot for receiving a purse string suture attached to each of the staples, said central slot extending longitudinally along said housing and intersecting said transverse slots; and a staple pusher bar slidably mounted for longitudinal movement in said housing, and for engaging and bending the legs of each staple toward the tissue clamping surface to secure the staples and the purse string suture to the tissue.

7. The staple cartridge of claim 6, wherein: said pusher bar includes a series of opposed pairs of wedge-shaped protrusions corresponding to the staple receiving slots formed in said housing, each pair of wedge-shaped protrusions for engaging and bending a leg of a staple toward the tissue clamping surface into an overlapped configuration when said staple pusher bar is moved longitudinally relative to said housing.

8. The staple cartridge of claim 7, wherein:

each wedge-shaped protrusion has a staple forming edge slanted inwardly toward the center of said staple pusher bar for engaging and bending the staple legs inwardly toward each other as said staple pusher bar is moved relative to said cartridge.

9. The staple cartridge of claim 6, wherein:

each staple receiving slot is located between a pair of ridges which extend upwardly from the top of the housing.

10. The staple cartridge of claim 9, wherein:

each pair of ridges is separated by a depression from the next adjacent pair of ridges.

11. The staple cartridge of claim 9, wherein:

said elongated central slot opens into a longitudinal V-shaped groove defined by inclined surfaces which are sloped upwardly and outwardly from the central slot and terminate at the top of said ridges.

12. The staple cartridge of claim 6, wherein:

each staple includes an eyelet which extends in the opposite direction from the staple legs for receiving the purse string suture; and said housing includes a plurality of recesses at the bottom of said staple receiving slots for receiving the eyelets of the staples therein.

13. A surgical instrument for applying a plurality of staples attached to a purse string suture to tissue, comprising:

a plurality of staples;

a pair of elongated handles pivotally connected together, said handles supporting a pair of jaws for receiving the tissue therebetween;

a pair of staple cartridges mounted on said jaws, said cartridges having opposed tissue clamping surfaces for clamping the tissue therebetween;

a row of staple receiving slots formed in each of said cartridges, each slot receiving a staple with its legs pointing toward the tissue clamping surface of said cartridge;

a central slot extending along said tissue clamping surface of each staple cartridge for receiving a purse string suture connected to the staples in each of said staple receiving slots;

a staple pusher bar slidably mounted in each cartridge for engaging and bending the legs of each staple toward the tissue clamping surface of said cartridge upon movement of said staple pusher bar relative to said cartridge; and actuating means on one of said handles for sliding the pusher bar in each staple cartridge to bend the staple legs and secure the staples and the purse string suture to the tissue clamped between said cartridges;

wherein said actuating means comprises:

a staple actuating lever pivotally mounted on one of said handles;

means for connecting said staple actuating lever to the staple pusher bar in each of said cartridges; and said staple actuating lever being manually pivotable to displace said connecting means to move the staple pusher bar in each of said cartridges.

14. The surgical instrument of claim 13, which includes;

a locking member pivotally mounted on one of said handles and movable between a first position in which said staple actuating lever is locked against movement and a second position in which said staple actuating lever is unlocked for movement.

15. A surgical instrument for applying a purse string suture to tissue, comprising:

a pair of staple cartridges having opposed tissue clamping surfaces for clamping the tissue therebetween;

a row of staple receiving slots formed in each of said cartridges, each slot being adapted to receive a staple with its legs pointing toward the tissue clamping surface of said cartridge;

a central slot extending along said tissue clamping surface of each staple cartridge for receiving a purse string suture connected to the staples in each of said staple receiving slots;

a staple pusher bar slidably mounted in each cartridge for engaging and bending the legs of each staple toward the tissue clamping surface of said cartridge upon movement of said staple pusher bar relative to said cartridge; and actuating means for sliding the pusher bar in each staple cartridge to bend the staple legs and secure the staples and purse string suture to the tissue clamped between said cartridges;

wherein said pusher bar includes a series of opposed pairs of wedge-shaped protrusions corresponding to the staple receiving slots in said cartridge, each pair of wedge-shaped protrusions being adapted to engage and bend the legs of the staple toward the tissue clamping surface into an overlapped configuration when said staple pusher bar is moved longitudinally relative to said cartridge.

* * * * *